United States Patent
Ohishi

(10) Patent No.: US 10,568,587 B2
(45) Date of Patent: Feb. 25, 2020

(54) X-RAY DIAGNOSTIC APPARATUS, IMAGE PROCESSING APPARATUS, AND IMAGE PROCESSING METHOD

(71) Applicant: Canon Medical Systems Corporation, Otawara-shi (JP)

(72) Inventor: Satoru Ohishi, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 115 days.

(21) Appl. No.: 15/938,304

(22) Filed: Mar. 28, 2018

(65) Prior Publication Data

US 2018/0279970 A1    Oct. 4, 2018

(30) Foreign Application Priority Data

Mar. 28, 2017 (JP) .................. 2017-063712
Mar. 28, 2018 (JP) .................. 2018-061119

(51) Int. Cl.
*G06K 9/00* (2006.01)
*A61B 6/02* (2006.01)
(Continued)

(52) U.S. Cl.
CPC ............ *A61B 6/022* (2013.01); *A61B 6/40* (2013.01); *A61B 6/42* (2013.01); *A61B 6/4441* (2013.01); *A61B 6/466* (2013.01); *A61B 6/481* (2013.01); *A61B 6/486* (2013.01); *A61B 6/504* (2013.01); *A61B 6/507* (2013.01); *A61B 6/5205* (2013.01);
(Continued)

(58) Field of Classification Search
None
See application file for complete search history.

(56) References Cited

U.S. PATENT DOCUMENTS 6,408,201 B1 *   6/2002   Foo ................. A61B 5/055
                                                    324/300
2002/0133070 A1 *  9/2002  Huang ............. A61B 5/055
                                                    600/420
(Continued)

FOREIGN PATENT DOCUMENTS

JP    2006-87631    4/2006
JP    2014-104140   6/2014
(Continued)

*Primary Examiner* — Shervin K Nakhjavan
(74) *Attorney, Agent, or Firm* — Oblon, McClelland, Maier & Neustadt, L.L.P.

(57) ABSTRACT

An X-ray-diagnostic apparatus generates time-series first vessel images corresponding to a first direction, and generates second vessel image corresponding to a second direction. The apparatus generates third vessel images corresponding to the second direction, by transforming more than one piece out of the first vessel images based on a blood vessel shape in one of the first vessel images and a blood vessel shape in at least one of the second vessel image, the third vessel image corresponding to respective time phases of the first vessel images. The apparatus generates first color image corresponding to the first direction by using more than one piece out of the first vessel images, and generates second color image corresponding to the second direction by using more than one piece out of the third vessel images. The apparatus displays a stereoscopic image based on the first color-image and the second color image.

14 Claims, 16 Drawing Sheets

(51) Int. Cl.
*A61B 6/00* (2006.01)
*G06T 7/00* (2017.01)

(52) U.S. Cl.
CPC .............. *A61B 6/54* (2013.01); *G06T 7/0012* (2013.01); *G06T 7/0016* (2013.01); *G06T 2207/10024* (2013.01); *G06T 2207/10116* (2013.01); *G06T 2207/30101* (2013.01); *G06T 2207/30104* (2013.01)

(56) References Cited

U.S. PATENT DOCUMENTS

| | | | | |
|---|---|---|---|---|
| 2003/0191394 | A1* | 10/2003 | Simon | A61B 6/481 600/473 |
| 2005/0089143 | A1* | 4/2005 | Nakano | A61B 6/4441 378/98.12 |
| 2009/0067568 | A1* | 3/2009 | Hall | G06T 5/50 378/4 |
| 2009/0076369 | A1* | 3/2009 | Mistretta | A61B 6/482 600/407 |
| 2010/0004526 | A1* | 1/2010 | Wei | C07D 473/04 600/407 |
| 2011/0135177 | A1* | 6/2011 | Ohishi | A61B 6/481 382/130 |
| 2012/0307964 | A1* | 12/2012 | Hall | A61B 6/03 378/8 |
| 2014/0371578 | A1* | 12/2014 | Auvray | A61B 6/12 600/424 |
| 2015/0150526 | A1 | 6/2015 | Ohishi | |
| 2016/0015348 | A1 | 1/2016 | Ohishi | |
| 2016/0371862 | A1* | 12/2016 | Silver | G06T 11/008 |
| 2017/0367673 | A1* | 12/2017 | Ohishi | A61B 6/4441 |
| 2018/0040147 | A1* | 2/2018 | Alhrishy | A61B 6/02 |

FOREIGN PATENT DOCUMENTS

| | | |
|---|---|---|
| JP | 2014-200339 | 10/2014 |
| JP | 2014-233369 | 12/2014 |
| JP | 2015-112293 | 6/2015 |
| JP | 2015-126868 | 7/2015 |

* cited by examiner

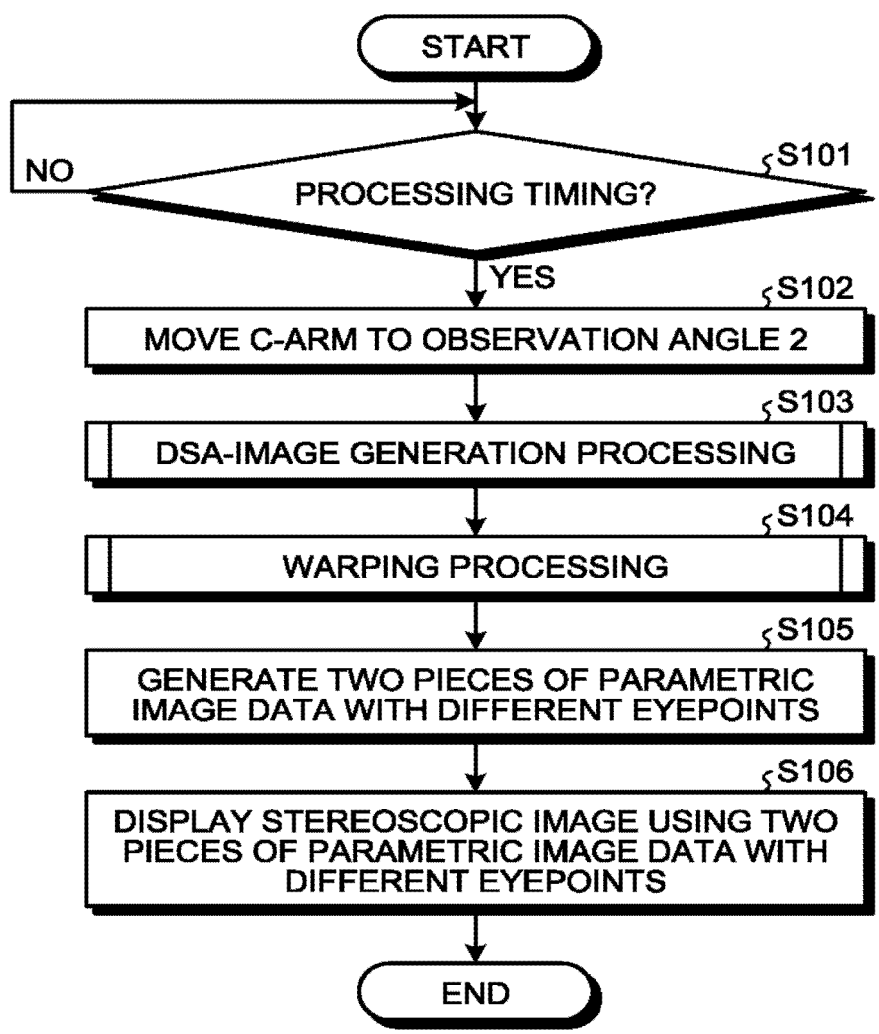

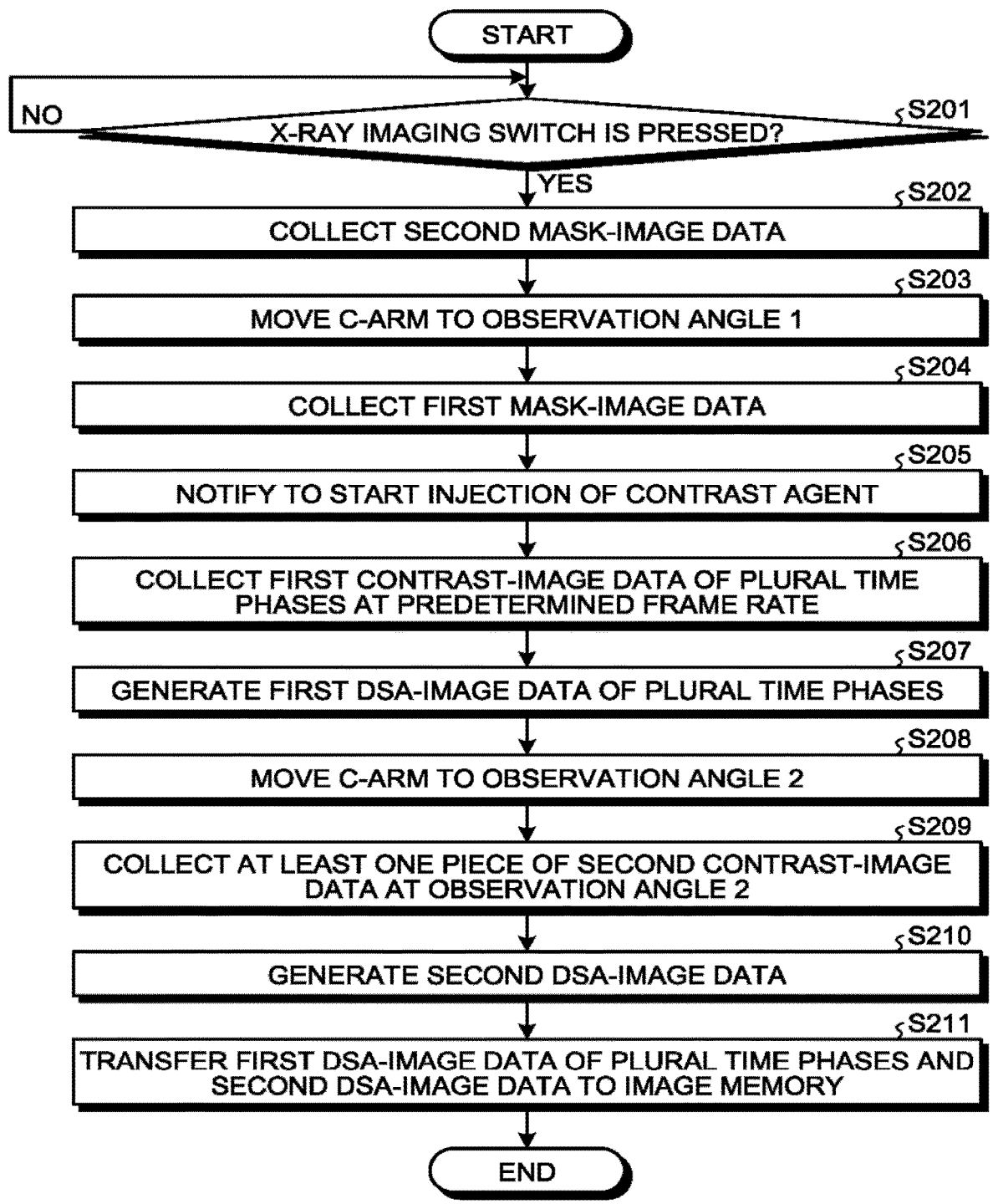

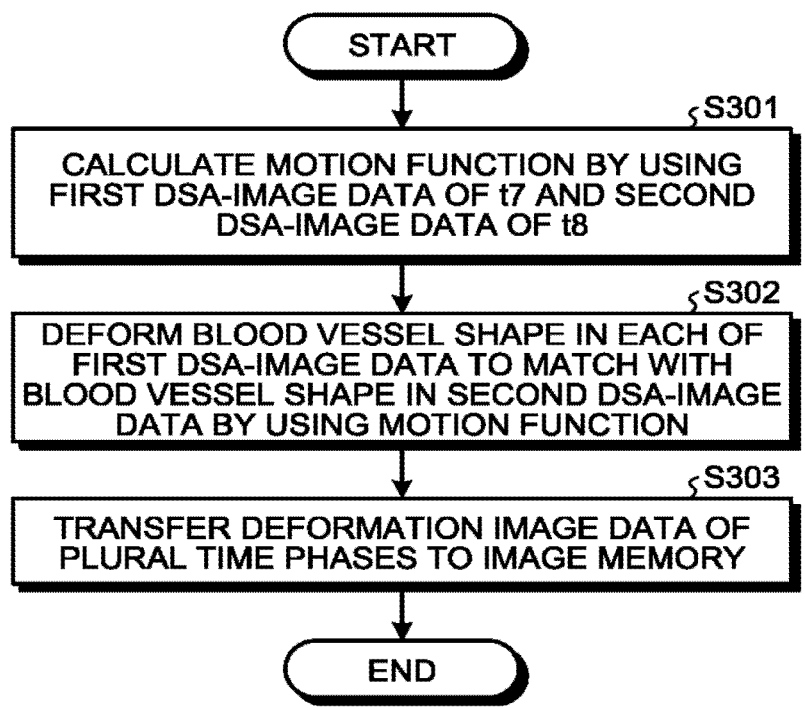

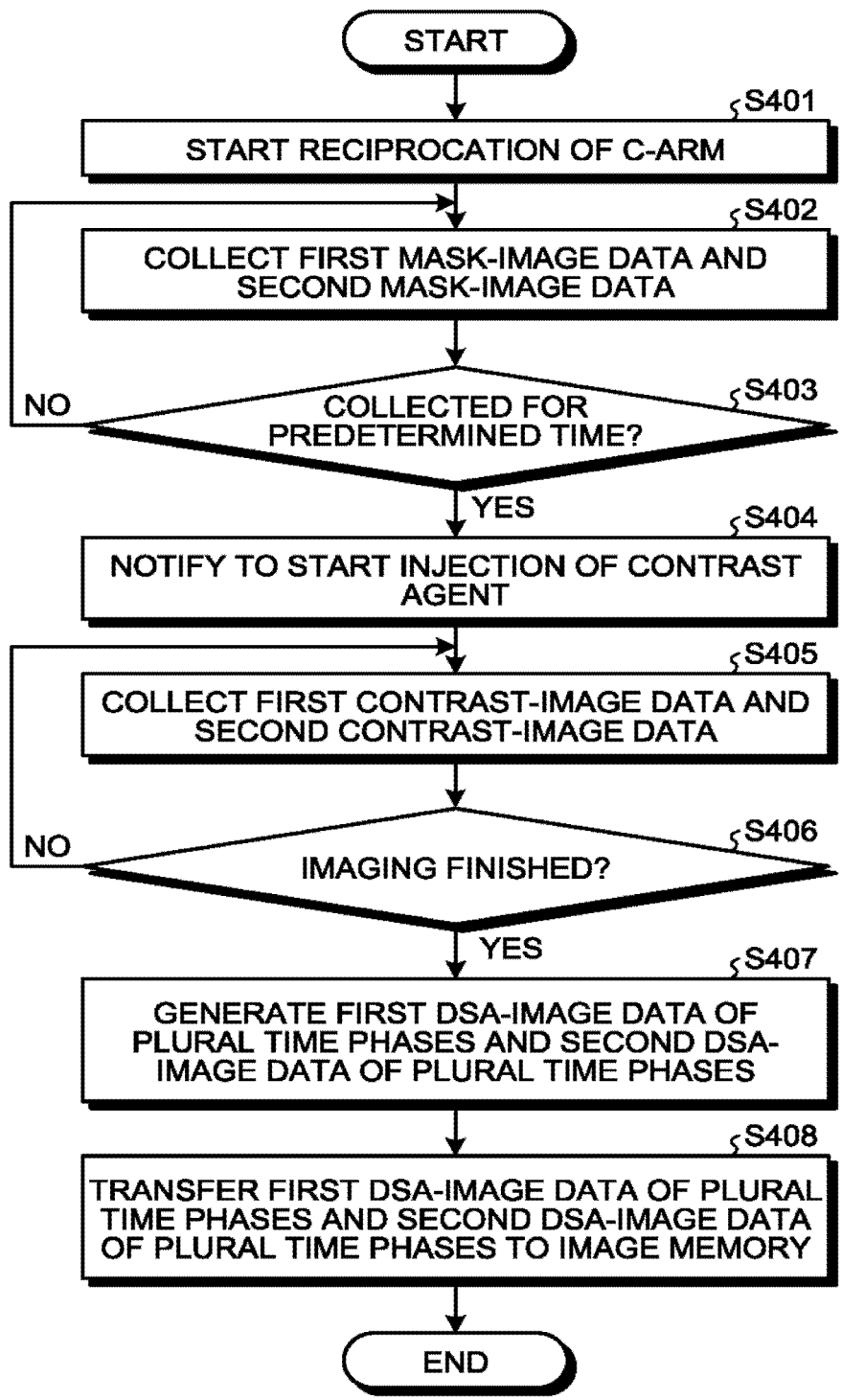

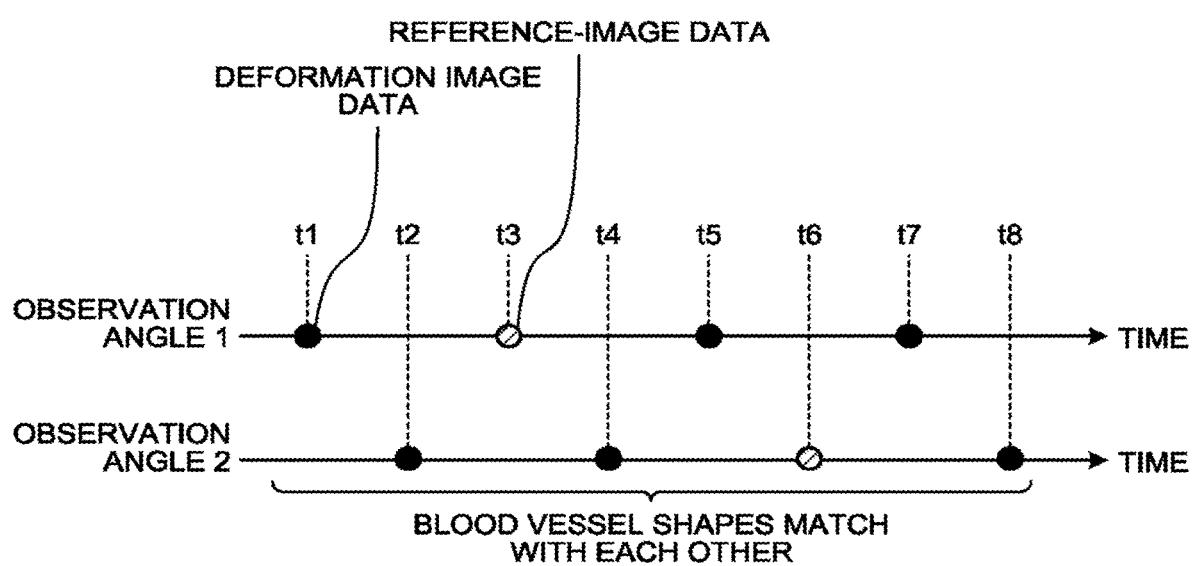

X-RAY DIAGNOSTIC APPARATUS, IMAGE PROCESSING APPARATUS, AND IMAGE PROCESSING METHOD

CROSS-REFERENCE TO RELATED APPLICATIONS

This application is based upon and claims the benefit of priority from Japanese Patent Application No. 2017-063712, filed on Mar. 28, 2017 and Japanese Patent Application No. 2016-061119, filed on Mar. 28, 2018; the entire contents of which are incorporated herein by reference.

FIELD

Embodiments described herein relate generally to an X-ray diagnostic apparatus, an image processing apparatus, and an image processing method.

BACKGROUND

Conventionally, digital subtraction angiography (DAS) has been known as angiography in an X-ray diagnostic apparatus. DSA is a technique of acquiring image data in which blood vessels that are visualized by a contrast agent are selectively rendered, by performing subtraction of X-ray image data before and after injection of the contrast agent to a subject. In DSA, for example, by acquiring an image before injection of a contrast agent, X-ray image data in the absence of contrast agent is collected as mask image data. Furthermore, by acquiring images while injecting the contrast agent, X-ray image data in the presence of contrast agent is collected as contrast image data. By subtraction processing between the mask image data and the contrast image data, DSA image data is generated.

Moreover, a technique called parametric imaging in which parameters relating to inflow time of the contrast agent are visualized into images by using DSA described above has been available. In the parametric imaging, for example, changes in pixel value at respective positions in DSA image data are regarded as changes in concentration of the contrast agent, and time used until the temporal change of a pixel value becomes at its peak, or reaches a predetermined value is calculated as inflow time. Furthermore, by mapping colors according to the calculated inflow time in the respective positions, parametric-imaging image data (also termed as "parametric image data") is produced in the parametric imaging.

Moreover, for X-ray diagnostic apparatuses, various techniques of providing stereoscopic X-ray image data have also been proposed. For example, a technique of imaging parallax images for right eye and left eye by changing the angle of a C-arm has been known.

BRIEF DESCRIPTION OF THE DRAWINGS

FIG. 3 is a flowchart illustrating a processing procedure of the X-ray diagnostic apparatus according to the first embodiment;

FIG. 4 is a flowchart illustrating a processing procedure of a DSA-image generation processing according to the first embodiment;

FIG. 6 is a flowchart illustrating a processing procedure of warping processing according to the first embodiment;

FIG. 8 is a flowchart illustrating a processing procedure of DSA-image generation processing according to a second embodiment;

FIG. 11A to FIG. 11C are diagrams for explaining the warping processing according to the second embodiment;

DETAILED DESCRIPTION

Figure 1:
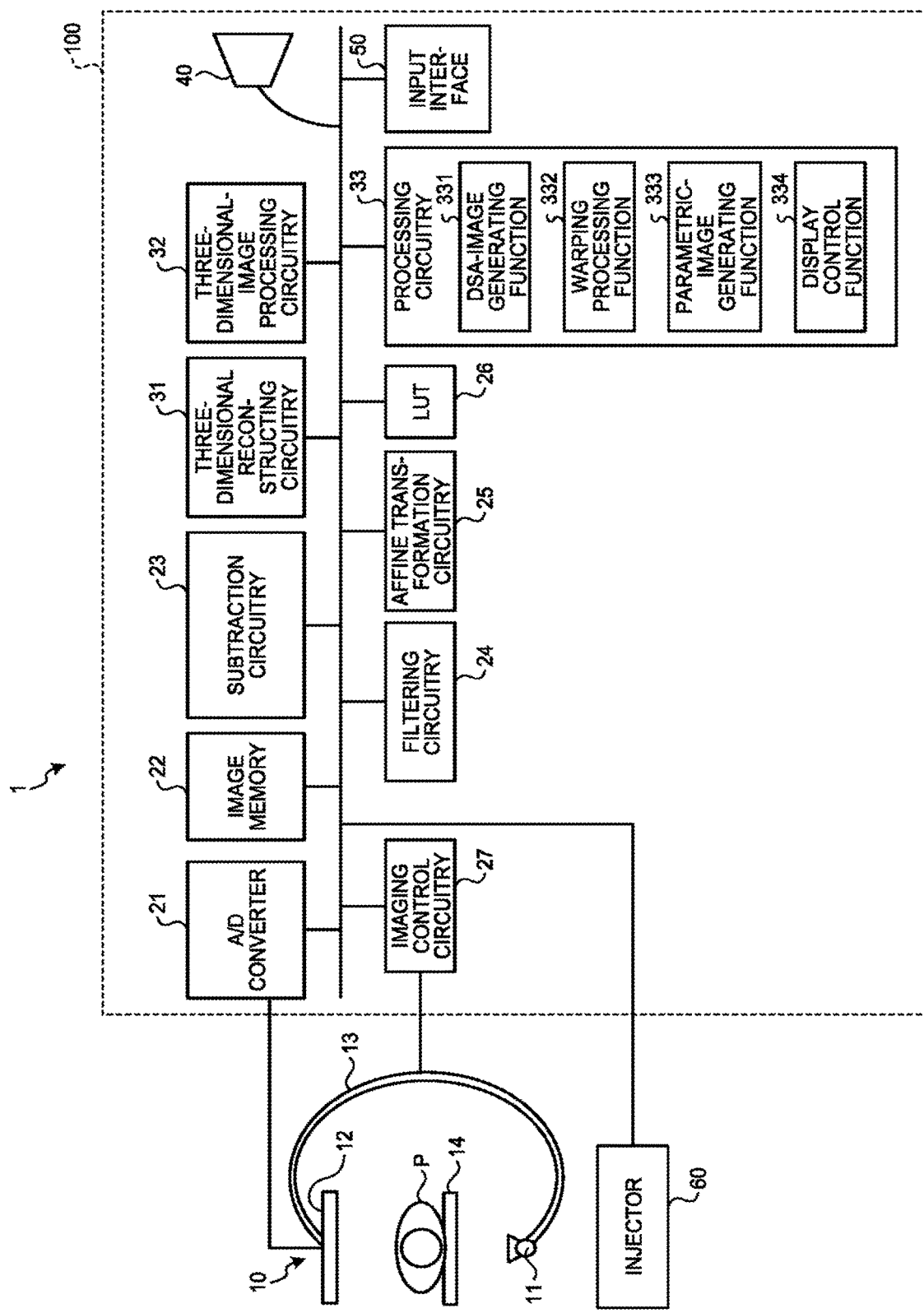
FIG. 1 illustrates one example of a configuration of an X-ray diagnostic apparatus according to a first embodiment.

An X-ray-diagnostic apparatus of an embodiment includes processing circuitry. The processing circuitry generates plural frames of time-series first vessel image data, whose observation direction is a first observation direction, and generates at least one frame of second vessel image data, whose observation direction is a second observation direction. The processing circuitry generates plural frames of time-series third vessel image data, whose observation direction is the second observation direction, by transforming more than one frame out of the plural frames of the time-series first vessel image data based on a blood vessel shape in at least one of the plural frames of the first vessel image data and a blood vessel shape in at least one of the second vessel image data. The processing circuitry generates first color image data, whose observation direction is a first observation direction, and that reflects a flow of a contrast agent by using the plural frames of the first vessel image data, and generates second color image data, whose observation direction is the second observation direction, and that reflects the flow of the contrast agent by using the plural frames of the third vessel image data. The processing circuitry causes a display to display a stereoscopic image based on the first color-image data and the second color image data.

In the following, an X-ray diagnostic apparatus, an image processing apparatus, and an image processing program according to embodiments are explained referring to the drawings. Embodiments are not limited to the following embodiments. Moreover, what is described in one embodiment is basically applied similarly to other embodiments also.

First Embodiment

FIG. 1 illustrates one example of a configuration of an X-ray diagnostic apparatus according to a first embodiment. As illustrated in FIG. 1, an X-ray diagnostic apparatus 1 according to the first embodiment includes an X-ray imaging mechanism 10 and an image processing apparatus 100.

The X-ray imaging mechanism 10 includes an X-ray tube 11, a detector (flat panel detector (FPD)) 12, a C-arm 13, and a bed 14, and an injector 60 is connected thereto The injector 60 is a device to inject a contrast agent through a catheter inserted into a subject P. Injection of the contrast agent from the injector 60 can be started according to an injection start instruction that is received through the image processing apparatus 100 described later, or can be started according to an injection start instruction that is directly input by an operator, such as a technologist, to the injector 60. Or there may be cases in which injection of contrast agent is performed manually by physicians via syringes.

The C-arm 13 supports the X-ray tube 11, and the detector 12 that detects X-rays irradiated from the X-ray tube 11. The C-arm 13 is rotated at a high speed as propellers around the subject F that is laid on the bed 14 by a motor not illustrated. The C-arm 13 is supported rotatably in three axes of X, Y, Z axes perpendicular to each other, and is rotated in each axis individually by a driving unit not illustrated. The C-arm 13 is one example of a supporting mechanism.

Figure 2A:
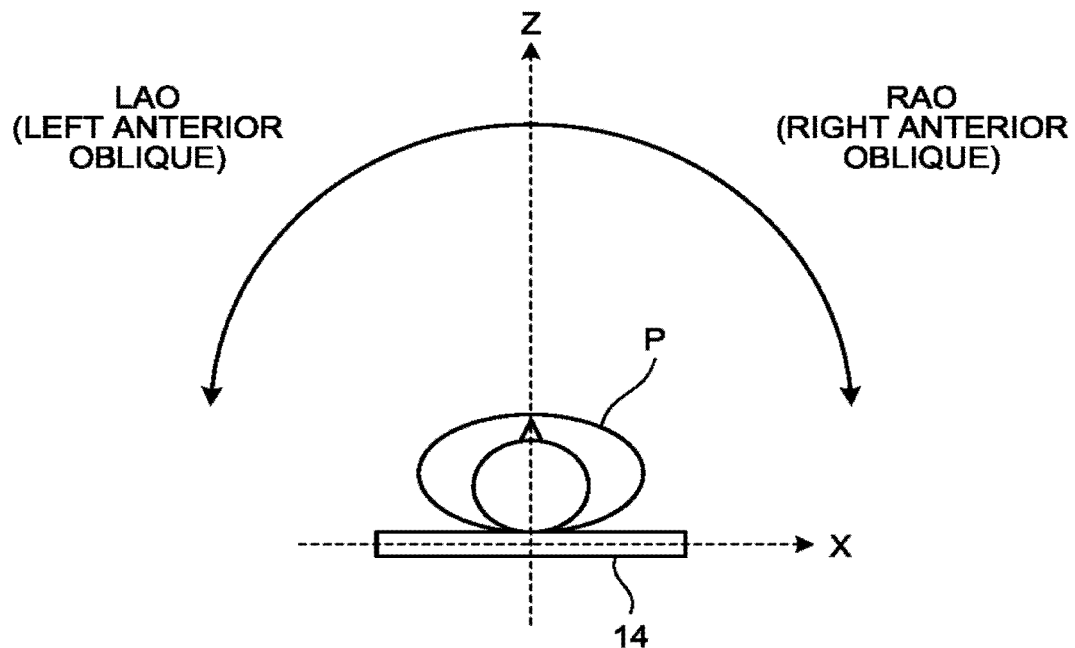
FIG. 2A and FIG. 2B are diagrams for explaining a rotation direction of a C-arm according to the first embodiment.
Figure 2B:
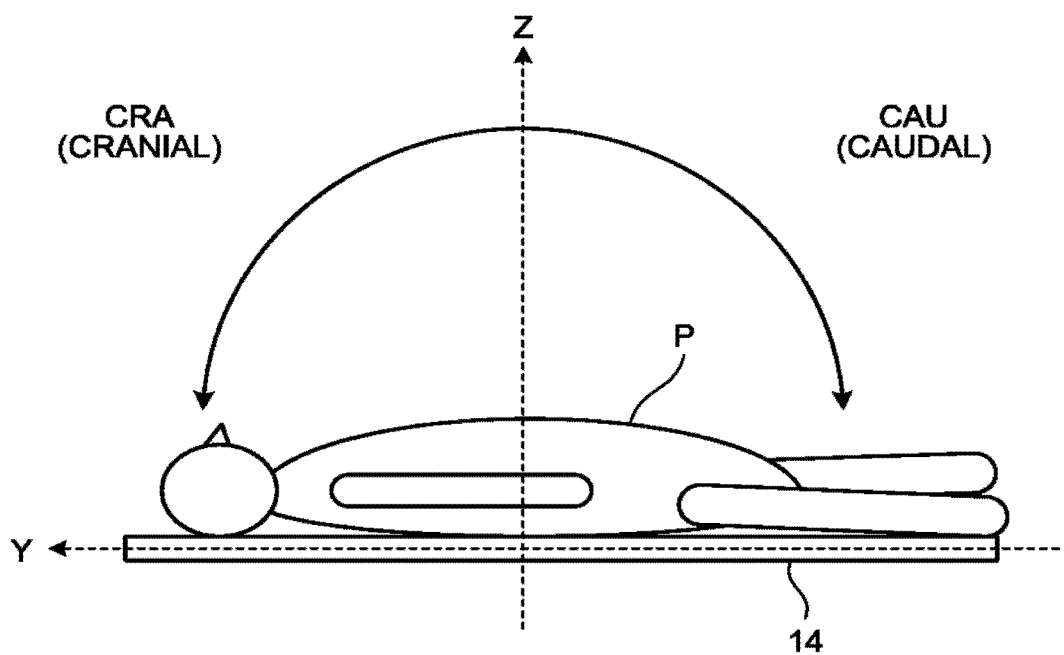

FIG. 2A and FIG. 2B are diagrams for explaining a rotation direction of the C-arm 13 according to the first embodiment. FIG. 2A illustrates the subject P viewed in a forward direction in the Z axis, and FIG. 2B illustrates the subject P viewed in a forward direction in the X axis.

As illustrated in FIG. 2A, rotation in a leftward direction of the subject P around the Z axis from the Y axis is called left anterior oblique (LAO), and rotation opposite to LAO is called right anterior oblique (RAO). Furthermore, as illustrated in FIG. 2B, rotation toward the Z axis from the XY plane is called cranial (CRA), and rotation opposite to CRA is called caudal (CAU). For example, when the X-ray detector 12 is positioned in a forward direction (that is, the front direction of a patient), the angle of the C-arm 13 is expressed as (RAO/LAO 0, CRA/CAU 0). This means that an RAO/LAO angle is 0 degree, and a CRA/CAU angle is 0 degree.

The X-ray tube 11 is an X-ray source that generates an X-ray be using high voltage supplied from a high-voltage generator not illustrated. The detector 12 is a device in which multiple X-ray detecting devices to detect an X-ray that has passed through the subject P are arranged in matrix. Each of the X-ray detecting devices included in this detector 12 outputs an X-ray that has passed through the subject P to an analog/digital (A/D) convertor 21 described later.

The image processing apparatus 100 includes the A/D convertor 21, an image memory 22, subtraction circuitry 23, filtering circuitry 24, affine transformation circuitry 25, a look up table (LUT) 26, imaging control circuitry 27, three-dimensional reconstructing circuitry 31, three-dimensional-image processing circuitry 32, processing circuitry 33, a display 40, and an input interface 50 as illustrated in FIG. 1.

The display 40 displays various kinds of information, such as various kinds of images processed by the image processing apparatus 100 and a graphical user interface (GUI). For example, the display 40 is a cathode ray tube (CRT) monitor or a liquid crystal monitor.

The display 40 is a display dedicated to stereoscopic views enabled to display a stereoscopic image that can provide a stereoscopic view based on image data for left eye and image data for right eye. For example, the display 40 has a structure in which a lenticular sheet with multiple lenses each having a substantially semi-cylindrical shape aligned, or a fly eye lens formed with many of lenses like a fly eye is attached on a display surface, and enables to observe a stereoscopic image with the naked eye by changing light path by the lens, without using stereoscopic glasses. The display 40 can be a display other than a naked eye dedicated stereoscopic display. In this case, the display 40 is a display that synchronizes with stereoscopic glasses, and while displaying image data for left eye, only a left glass of the glasses is allowed to pass light and a right glass thereof is not allowed to pass light. On the other hand, while displaying image data for right eye, only the right glass of the glasses is allowed to pass light and the left glass thereof is not allowed to pass light. Alternatively, the display 40 has a structure in which a polarization filter is attached on a display surface and, for example, horizontal polarization is applied to even pixel lines and vertical polarization is applied to odd pixel lines. A left eye side of the stereoscopic glasses is structured to pass only horizontally polarized light and a right eye side thereof is structured to pass only vertically polarized light, and image data for left eye is displayed on even pixel lines, and image data for right eye is displayed on odd pixel lines. By thus using glasses dedicated to stereoscopic views, X-ray image data enabling to have a stereoscopic view is displayed. The image data for left eye and the image data for right eye are defined by viewing angles.

The input interface 50 corresponds to an input device, such as a mouse, a keyboard, a button, a panel switch, a touch command screen, a foot switch, a trackball, and a joystick. The input interface 50 accepts various kinds of instructions from an operator, and transfers the accepted instructions to respective circuits of the image processing apparatus 100 as appropriate.

Moreover, for example, the input interface 50 includes an X-ray trigger button to instruct irradiation of an X-ray. When the X-ray trigger button is pressed by an operator, the X-ray diagnostic apparatus 1 starts imaging to acquire X-ray image data. Furthermore, for example, the input interface 50 includes a device driving button to instruct a change of an irradiation direction of an X-ray. When the device driving button is pressed by an operator, the X-ray diagnostic apparatus 1 changes the irradiation direction of an X-ray by rotating the C-arm 13 toward a direction set in advance.

The A/D convertor 21 is connected to the detector 12, and converts an analog signal input from the detector 12 into a digital signal, and stores the converted digital signal in the image memory 22 as X-ray image data.

The image memory 22 stores the X-ray image data. Moreover, the image memory 22 stores reconstruction data (volume data) that is reconstructed by the three-dimensional reconstructing circuitry 31 described later, or a three-dimensional image that is generated by the three-dimensional-image processing circuitry 32. The image memory 22 can also store a computer-executable program.

The subtraction circuitry 23 generates subtraction image data, such as DSA image data. For example, the subtraction circuitry 23 generates DSA image data by using mask image data and contrast image data stored in the image memory 22, or generates volume data including a blood vessel structure by using two pieces of volume data. The mask image data corresponds to X-ray image data (non-contrast image data) that is imaged before injection of a contrast agent. Furthermore, the contrast image data corresponds to X-ray image data (contrast image data) that is imaged while injecting a contrast agent.

The filtering circuitry 24 performs image processing filtering such as high-pass filtering, low-pass filtering, or the like. The affine transformation circuitry 25 scales up or down an image, and move an image. The LUT 26 stores a table to perform tone conversion.

The imaging control circuitry 27 controls various kinds of processing relating to imaging by the X-ray imaging mechanism 10 under control of the processing circuitry 33 described later. For example, the imaging control circuitry 27 controls rotation imaging in which X-ray images are imaged at predetermined frame rate while rotating the C-arm 13. As an example, the imaging control circuitry 27 controls the rotation imaging of X-ray image data performed more than once after injection of a single contrast agent, based on a signal that is output from the injector 60 when the injection of the contrast agent is started as a trigger. The imaging control circuitry 27 controls a start of the rotation imaging performed multiple times based on elapsed time from an injection start time of the single contrast agent, thereby performing rotation imaging synchronized with arrival of the contrast agent at a target of the rotation imaging.

Moreover, the imaging control circuitry 27 controls a high voltage generator not illustrated to generate an X-ray continuously or intermittently from the X-ray tube 11, and controls the detector 12 to detect an X-ray that has passed through the subject P while controlling the rotation of the C-arm 13. The imaging control circuitry 27 causes the X-ray tube 11 to generate an X-ray based on an X-ray generation condition that is set by the processing circuitry 33 described later for each rotation imaging. In other words, the X-ray imaging mechanism 10 serving as an imaging mechanism includes an X-ray tube that generates an X-ray and a detector that detects the X-ray, and movably holds at least the X-ray tube so that the observation direction by an X-ray is changeable. Furthermore, the imaging control circuitry 27 serving as an imaging control unit controls the observation direction by the imaging mechanism, and imaging performed by the X-ray tube and the detector.

The three-dimensional reconstructing circuitry 31 reconstructs reconstruction data (volume data) from X-ray images collected by the rotation imaging performed by the X-ray imaging mechanism 10. For example, the three-dimensional reconstructing circuitry 31 reconstructs volume data including a vessel structure from projection data subjected to subtraction that is obtained by performing subtraction by the subtraction circuitry 23 between rotation X-ray image data as mask image data and an X-ray image substantially matching in angle with the mask image data in a rotation X-ray image as a contrast image, and that is stored in the image memory 22. Alternatively, the three-dimensional reconstructing circuitry 31 reconstructs volume data using rotation X-ray image data as mask image data stored in the image memory 22, and volume data using rotation X-ray image data as contrast image data separately, and generates volume data including a vessel structure by performing subtraction between the two pieces of volume data. Subsequently, the three-dimensional reconstructing circuitry 31 stores the reconstructed volume data in the image memory 22.

The three-dimensional-image processing circuitry 32 generates three-dimensional medical-image data from the volume data stored in the image memory 22. For example, the three-dimensional-image processing circuitry 32 generates volume-rendering image data or multiplanar reconstruction (MPR) image data from the volume data. Subsequently, the three-dimensional-image processing circuitry 32 stores the generated three-dimensional medical-image data in the image memory 22. Moreover, the three-dimensional-image processing circuitry 32 refers to the LUT 26 and performs tone conversion of the three-dimensional medical-image data.

The processing circuitry 33 controls the entire X-ray diagnostic apparatus 1. Specifically, the processing circuitry 33 controls various kinds of processing relating to imaging of X-ray image data by the X-ray imaging mechanism 10, generation of a display image, display of a display image on the display 40, and the like. For example, the processing circuitry 33 causes the X-ray imaging mechanism 10 to perform rotation imaging, generates three-dimensional image data from X-ray image data acquired by the rotation imaging, and displays it on the display 40.

Furthermore, the processing circuitry 33 performs a parametric-image generating function 333 and a display control function 334 as illustrated in FIG. 1. The parametric-image generating function 333 and the display control function 334, which are components of the processing circuitry 33 illustrated in FIG. 1, are stored in a storage device (for example, the image memory 22) of the X-ray diagnostic apparatus 1, for example, in a form of computer-executable program. The processing circuitry 33 is a processor that reads and executes respective programs from the storage device to implement functions corresponding to the respective programs. In other words, the processing circuitry 33 that has read the respective program is to have the respective functions indicated in the processing circuitry 33 illustrated in FIG. 1.

Note that what is illustrated in FIG. 1 is only one example. For example, although plural circuits (processors) of the subtraction circuitry 23, the filtering circuitry 24, the affine transformation circuitry 25, the imaging control circuitry 27, the three-dimensional reconstructing circuitry 31, the three-dimensional-image processing circuitry 32, and the processing circuitry 33 are illustrated in FIG. 1, these circuits are not necessarily required to be configured independently. For example, arbitrary circuits out of these circuits can be combined.

The term "processor" used in the above explanation signifies, for example, a central processing unit (CPU), a graphics processing unit (GPU), or a circuit such as an application specific integrated circuit (ASIC), a programmable logic device (for example, simple programmable logic device (SPLD), complex programmable logic device (CPLD)), and a field programmable gate array (FPGA). The processor reads and executes a program stored in a storage circuit, and thereby implements a function. Instead of storing a program in the storage circuit, the program can be directly installed in a circuit of the processor. In this case, the processor reads and executes the program installed in the circuit of the processor to implement the function. The respective processors in the present embodiment are not limited to be structured as an independent circuit per processor, but can be structured by combining multiple independent processors to form a single processor to implement the functions. Furthermore, more than one component in each drawing can be integrated to a single processor to implement the functions.

As above, one example of the configuration of the X-ray diagnostic apparatus 1 according to the first embodiment has been explained. In the X-ray diagnostic apparatus 1 configured as describe above, the processing circuitry 33 performs a DSA-image generating function 331, a warping processing function 332, the parametric-image generating function 333, and the display control function 334 for facilitated provision of a stereoscopic image in parametric imaging.

That is, the DSA-image generating function 331 generates first subtraction-image data by subtracting first non-contrast-image data corresponding to the first observation direction from first contrast-image data corresponding to the first observation direction. Moreover, the DSA-image generating function 331 generates second subtraction-image data by subtracting second non-contrast-image data corresponding to the second observation direction from second contrast-image data corresponding to the second observation direction at is different from the first observation direction. The DSA-image generating function 331 is one example of a subtraction-image generating unit. Moreover, the DSA-image generating function 331 is one example of a vessel-image generating unit.

Subsequently, the warping processing function 332 performs transformation processing to transform a blood vessel shape that is drawn in image data other than reference image data based on a blood vessel shape drawn in the reference image data that is to be reference out of the first subtraction-image data and the second subtraction-image data. The warping processing function 332 is one example of an image processing unit.

Subsequently, the parametric-image generating function 333 generates first color-image data that corresponds to the first observation direction and in which colors are allocated according to temporal changes in pixel value, and second color-image data that corresponds to the second observation direction and in which colors are allocated according to temporal changes in pixel value, using image data subjected to the transformation processing. The parametric image generating function 333 is one example of a color-image generating unit.

The display control function 334 displays a stereoscopic image based on the first color-image data and the second color-image data. Thus, the X-ray diagnostic apparatus 1 is enabled to provide a stereoscopic image in parametric imaging with ease. The display control function 334 is one example of a display control unit.

The respective functions performed by the processing circuitry 33 are set in advance, for example, as an imaging program for X-ray parametric imaging (hereinafter, also "imaging program"). For example, in the imaging program, a parallactic angle is registered in advance. The parallactic angle is an angle to determine positions (observation angle 1, observation angle 2) of two eyepoints that are set for stereo observation.

For example, when the C-arm 13 is set to an angle of RAO30CRA0, RAO30CRA0 is observation angle 1, and RAO35CRA0 further rotated by 5 degrees rightward from observation angle 1 is observation angle 2. This rotation direction is preferable to be changed according to a running direction of a blood vessel to be observed. Therefore, an imaging program can be prepared for each rotation direction, or the imaging program can include a GUI to determine a direction prepared therein, and the GUI can be used to determine rotation direction. As an example, the C-arm 13 rotates 5 degrees in the LAO direction when a joystick is tilted rightward, in the RAO direction when tilted leftward, in the CRA direction when tilted upward, and in the CAU direction when tilted downward (the rotation direction changes without changing the angle). Specifically, when the joystick is tilted upward from RAO30CRA0, RAO30CRA0 is set to observation angle 1, and when tilted upward from RAO30CRA0, RAO30CRA5 that is at an angle rotated by 5 degrees upward from RAO30CRA0 is set to observation angle 2. Alternatively, when the joystick is tilted rightward from RAO30CRA0, RAO30CRA0 is set to observation angle 1, and RAO25CRA0 that is an angle rotated by 5 degrees leftward from RAO30CRA0 is set to observation angle 2. In this example, for clear explanation, the case in which the joystick is tilted toward either one of upward, downward, leftward, and rightward has been explained, any complex direction (oblique direction) combining, for example, an upward direction and a rightward direction can be designated as the rotation direction.

FIG. 3 is a flowchart illustrating a processing procedure of the X-ray diagnostic apparatus 1 according to the first embodiment. The processing procedure illustrated in FIG. 3 is performed in angiographic or interventional procedures. In the first embodiment, a case of targeting a part that moves rarely, such as intracranial vessels is explained.

As illustrated in FIG. 3, the processing circuitry 33 determines whether it is time to perform processing (step S101). For example, when an instruction to start the imaging program is input by an operator, the processing circuit determines that it is time to start processing, and performs processing at step S102 and later. When negative determination is made at step S101, the processing circuitry 33 does not start imaging, and the following processing is suspended.

Subsequently, the processing circuitry 33 moves the C-arm 13 to observation angle 2 (step S102). Next, the DSA-image generating function 331 performs DSA-image generation processing (step S103). By this DSA-image generation processing, first DSA-image data and second DSA-image data are generated. The first DSA-image data is DSA image data corresponding to observation direction 1. Moreover, the second DSA-image data is DSA image data corresponding to observation angle 2. The DSA image data (subtraction image data) is an example of subtraction image data. Furthermore, the DSA-image data is an example of vessel image data.

Figure 5A:
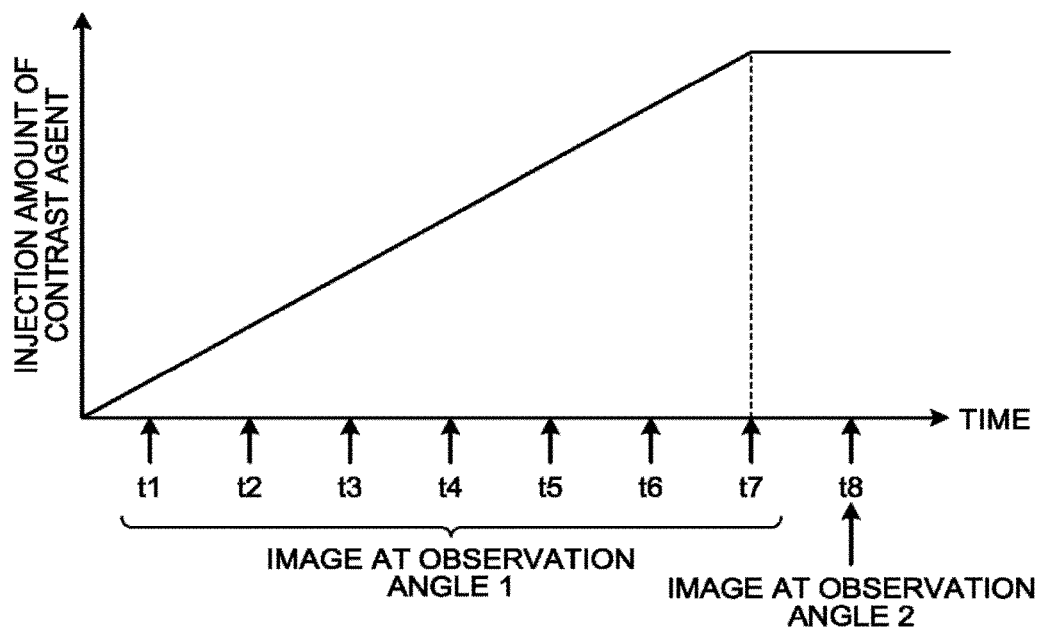
FIG. 5A and FIG. 5B are diagrams for explaining the DSA-image generation processing according to the first embodiment.
Figure 5B:
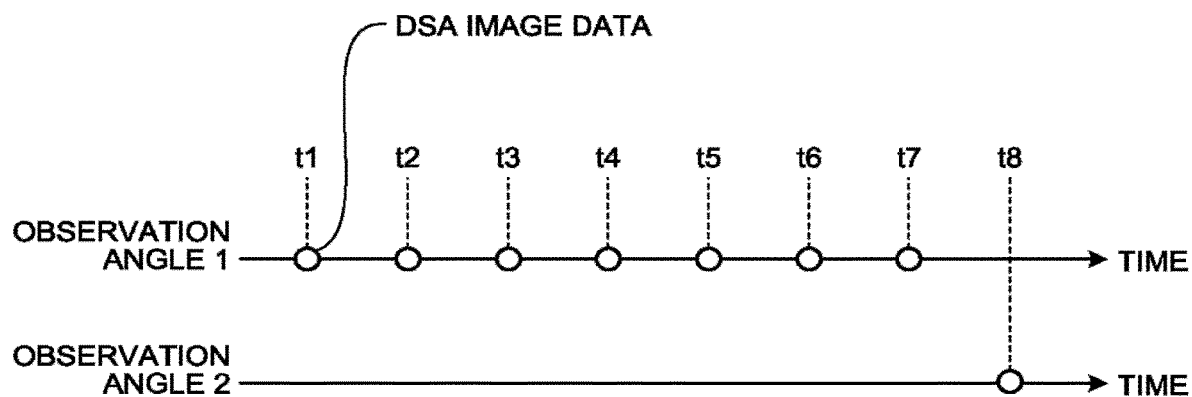

The DSA-image generation processing is explained wing FIG. 4, FIG. 5A, and FIG. 5F. FIG. 4 is a flowchart illustrating a processing procedure of the DSA-image generation processing according to the first embodiment. FIG. 4 illustrates the processing procedure corresponding to the DSA-image generation processing at step S102 in FIG. 3. FIG. 5A and FIG. 5E are diagrams for explaining the DSA-image generation processing according to the first embodiment. In FIG. 5A, a horizontal axis is for time, and a vertical axis is for an injection amount of a contrast agent. In FIG. 5B, a horizontal axis is for time. In FIG. 5B, a circle expresses DSA image data at that point of time.

As illustrated in FIG. 4, the DSA-image generating function 331 determines whether an X-ray imaging switch (X-ray trigger button) is pressed (step S201). For example, when the X-ray imaging switch is pressed by an operator (step S201: YES), the DSA-image generating function 331 start processing at step S202 and later. Until the X-ray trigger button is pressed (step S201: NO), the DSA-image generating function 331 does not start the processing at step S202 and later. Moreover, it is preferable that the operator should make preparations for injecting a contrast agent, such as filling the contrast agent in an injector or syringe.

When the X-ray imaging switch is pressed, the DSA-image generating function 331 collects second mask-image data step S202). The second mask-image data is mask image data corresponding to observation angle 2. For example, the DSA-image generating function 331 controls devices of an imaging system, such as the X-ray tube 11 and the detector 12, and to collects a predetermined number of the second mask-image data in the imaging program. The number of the second mask-image data can be one or more. The number of the second mask-image data is set according to a noise level necessary for the mask image data. The number of the second mask-image data is set in advance in the imaging program. The DSA-image generating function 331 moves the C-arm 13 to observation angle 1 (step S205).

Subsequently, the DSA-image generating function 331 collects first mask-image data (step S204). The first mask-image data is mask image data corresponding to observation angle 1. For example, the DSA-image generating function 331 collects the first mask-image data by similar processing to the processing at step S202.

The DSA-image generating function 331 then notifies to start injection of a contrast agent (step S205). For example, the DSA-image generating function 331 displays an icon indicating injection start timing on a screen of the display 40, thereby notifying to start injection of the contrast agent. Not limited thereto, notification to start the injection can be done by sound output, or by displaying a count-down timer that indicates the injection start timing. Thus, the operator starts injection of the contrast agent using a syringe. Alternatively, by using the injector 60, injection of the contrast agent can be automatically started after collection of the first mask-image data is completed.

The DSA-image generating function 331 then collects first contrast-image data of plural time phases at a predetermined frame rate (step S206). The first contrast-image data is contrast image data corresponding to observation angle 1.

As illustrated in FIG. 5A, for example, the DSA-image generating function 331 starts collecting the first contrast-image data at a framerate of 10 frames per second (fps). Subsequently, the DSA-image generating function 331 acquires seven frames of the first contrast-image data in total at t1, t2, t3, t4, t5, t6, and t7. The frame rate for collecting the first contrast-image data is preferable to be changed according to a blood flow rate of a target part. For example, it is set to 60 fps for a part with a high blood flow rate, and is set to 6 fps for a part with a low blood flow rate.

The DSA-image generating function 331 then generates first DSA-image data of plural time phases (step 207). As illustrated in FIG. 5B, for example, the DSA-image generating function 331 controls the subtraction circuitry 23 to subtract the first mask-image data from each of the seven frames of the first contrast-image data corresponding to t1 to t7, thereby generating seven frames of the first DSA-image data corresponding to t1 to t7. When plural frames of the first mask-image data are present, it is preferable that first mask-image data with reduced noises be generated by averaging the plural frames of the first mask-image data. The generated first DSA-image data is displayed on the display 40 by the display control function 334 in substantially real time.

Subsequently, the DSA-image generating function 331 moves the C-arm 13 to observation angle 2 (step S208). For example, while observing the first DSA-image data displayed on the display 40, the operator presses an observation-angle changing switch when the contrast agent is still sufficiently present in a blood vessel (artery) and a target part is contrasted. Thus, the DSA-image generating function 331 suspends X-ray irradiation, and moves the C-arm 13 to observation angle 2.

The DSA-image generating function 331 then collects at least one frame of second contrast-agent data (step S209). As illustrated in FIG. 5A, for example, the DSA-image generating function 331 acquires at least one frame of the second contrast-image data right upon moving the C-arm 13 to observation angle 2. As for the second contrast-image data, one frame is enough if a blood vessel shape is drawn therein, but plural frames can be acquired to reduce noises. However, even when acquiring plural frames, it is preferable to limit the number to about three frames. Imaging by the DSA-image generating function 331 is controlled by the imaging control circuitry 27. That is, the imaging control circuitry 27 images to acquire plural frames of time-series first contrast-image data in a state in which the observation direction of the imaging mechanism is set to the first observation direction, and after acquisition of the first contrast-image data, at least one frame of the second contrast-image data at the second observation direction. For example, the imaging control circuitry 27 acquires plural frames of the first contrast-image data within predetermined time since start of injection of a contrast agent, and shifts to the second observation direction after the predetermined time passes since the start of injection of the contrast agent and acquires at least one frame of the second contrast-image data before or just after completion of injection.

Subsequently, the DSA-image generating function 331 generates the second DSA-image data (step S210). As illustrated in FIG. 5B, for example, the DSA-image generating function 331 controls the subtraction circuitry 23, to subtract the second mask-image data from one frame of the second contrast-image data corresponding to t8, thereby generating one frame of the second DSA-image data corresponding to t8. When plural frames of the second mask-image data are present, it is preferable that second mask-image data with reduced noises be generated by averaging the plural frames of the second mask-image data. Furthermore, when plural frames of the second contrast-image data are present, it is preferable that second contrast image data with reduced noises be generated by averaging the plural frames of the second contrast-image data. The generated second DSA-image data is displayed on the display 40 by the display control function 334 in substantially real time.

In other words, the DSA-image generating function 331 serving as a vessel-image generating unit generates plural frames of first vessel-image data based on plural frames of the first contrast-image data, and generates one frame of second vessel-image data based on at least one frame of the second contrast-image data. For example, the DSA-image generating function 331 generates plural frames of the first vessel-image data by subtracting the first non-contrast-image data, whose observation direction is the first observation direction, from each of the plural frames of the first contrast-image data. Moreover, the DSA-image generating function 331 generates the second vessel-image data, by subtracting second non-contrast-image data, whose observation direction is the second observation direction, from at least one frame of the second contrast-image data.

Subsequently, the DSA-image generating function 331 transfers the first DSA-image data of plural time phases and the second DSA-image data to the image memory 22 (step 211). For example, the DSA-image generating function 1 transfers (stores) seven frames of the first DSA-image data corresponding to t1 to t7 and one frame of the second DSA-image data corresponding to t8 to the image memory 22.

The processing procedure illustrated in FIG. 4 is only one example, and it is not limited to the illustrated example. For example, the order in the processing procedure illustrated in FIG. 4 can be changed arbitrarily within a range not causing a contradiction in the processing. For example, the processing of generating the first DSA-image data (step S207) can be performed simultaneously with the processing of generating the second DSA-image data (step S210). Moreover, the processing of transferring the DSA image data (step S211) can be performed in parallel with the processing of generating the DSA image data.

Furthermore, although the case in which change of an observation angle to be performed after injection of a contrast agent (step S209) is performed in response to an instruction (depression of the observation-angle changing switch) by an operator has been explained in FIG. 4, it is not limited thereto. For example, it is assumed that a sufficient amount of contrast agent is present in a blood vessel soon after injection of the contrast agent is completed, and that a target part is contrasted. Therefore, the C-arm 13 can be automatically moved to observation angle 2 when predetermined time (for example, 5 seconds) has passed since start of injection of the contrast agent is notified (step S205). As time for injecting a contrast agent is substantially dependent on an amount of the contrast agent to be injected, the time can be set in advance according to an amount of the contrast agent or a target part. Moreover, when a contrast agent is injected by using the injector 60, the C-arm 13 can be automatically moved to observation angle 2 another predetermined time before an injection finish time of the contrast agent. The second predetermined time is preferable to be changed according to a blood flow rate at a target part. For example, it is set to 3 seconds for a part with a high blood flow rate, and it is set to 1 second for a part with a low blood flow rate. That is, the DSA-image generating function 331 collects the first contrast-image data of plural time phases from an injection start time of the contrast agent, and shifts to the second observation direction before predetermined time passes since completion of injection of the contrast agent to collect the second contrast-image data. In other words, the DSA-image generating function 331 serving as the vessel-image generating unit generates plural frames of time-series first vessel-image data, whose observation direction is the first observation direction, and generates one frame of second vessel-image data, whose observation direction is the second observation direction. For example, the imaging control circuitry 27 acquires the first contrast-image data of plural time phases since start of injection of a contrast agent, and shifts to the second observation direction before predetermined time passes since completion of injection of the contrast agent and acquires the second contrast-image data.

Furthermore, what is illustrated in FIG. 5A and FIG. 5B is only one example, and it is not necessarily limited to the illustrated example. For example, the number of frames of the first DSA-image data and the second DSA-image data is not limited to one in the illustrated example, and can be set to any number.

Explanation returns to FIG. 3. When the first DSA-image data and the second DSA-image data are generated, the warping processing function 332 performs warping processing (step S104). The warping processing function 332 performs warping processing to match a blood vessel shape of another image data to a blood vessel shape to be a reference out of blood vessel shapes drawn in the first DSA-image data and the second DSA-image data. The warping processing is an example of the transformation processing.

Figure 7A:
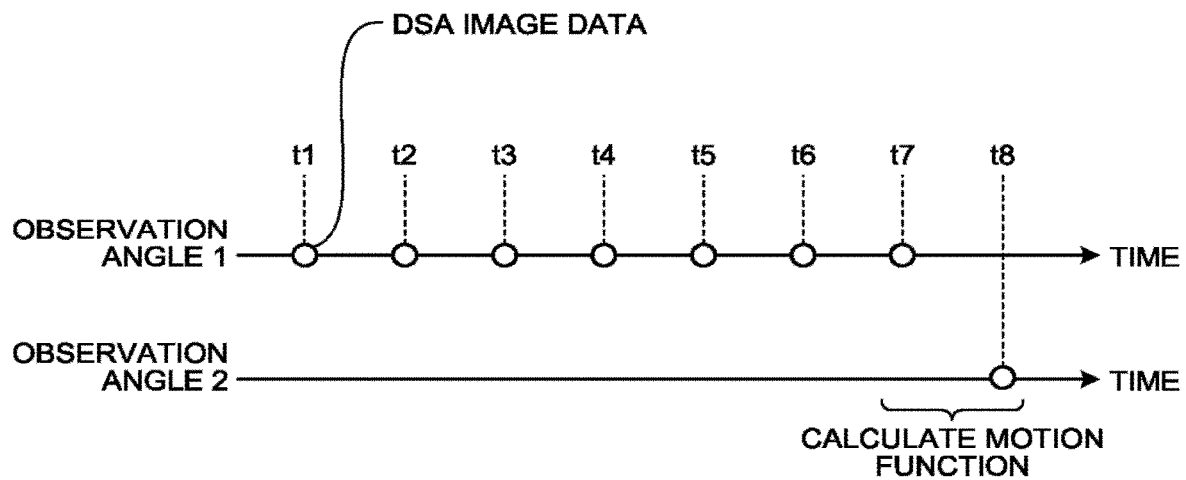
FIG. 7A and FIG. 7B are diagrams for explaining the warping processing according to the first embodiment.
Figure 7B:
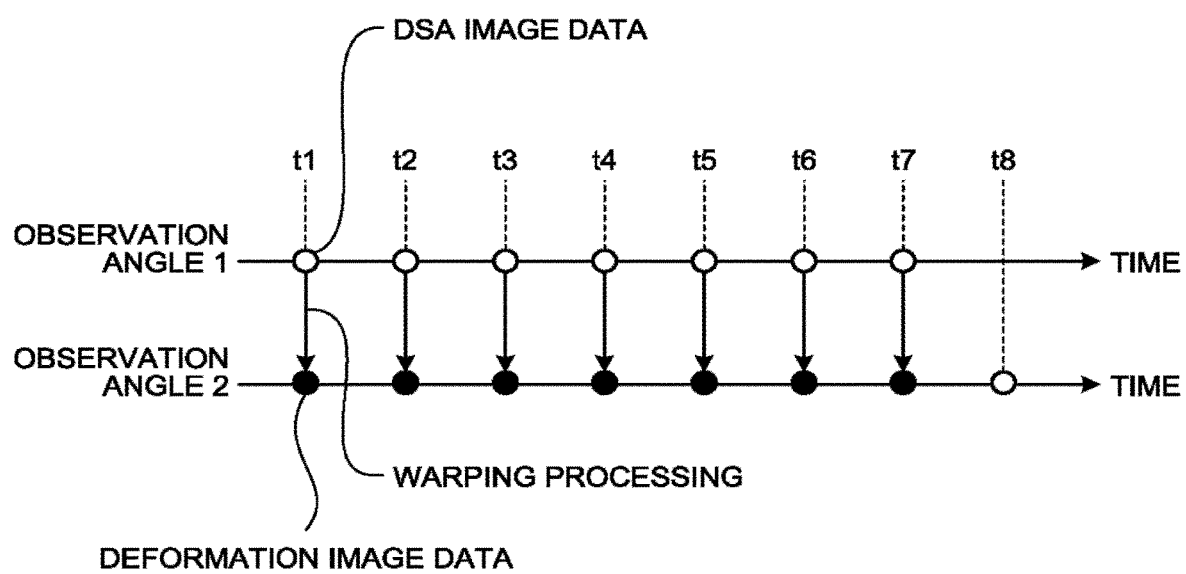

The warping processing is explained using FIG. 6, FIG. 7A, and FIG. 7B. FIG. 6 is a flowchart illustrating a processing procedure of the warping processing according to the first embodiment. FIG. 6 illustrates a processing procedure corresponding to the warping processing at step S104 in FIG. 3. FIG. 7A and FIG. 7B are diagrams for explaining the warping processing according to the first embodiment. In FIG. 7A and FIG. 7E, a horizontal axis is for time. Moreover, in FIG. 7A and FIG. 7B, a white circle expresses DSA image data at that point, and a black circle expresses transformation image data at that point. The transformation image data is image data that is transformed by the warping processing.

As illustrated in FIG. 6 and FIG. 7A, the warping processing function 332 calculates a motion function (motion vector) by using the first DSA-image data at t7 and the second DSA-image data at t8 (step S301). The motion function expresses a positional relationship to move respective pixels so as to match a blood vessel shape drawn in one image data to a blood vessel shape of another. For example, the warping processing function 332 calculates a motion function by performing local pattern matching between the first DSA-image data of t7 and the second DSA-image data of t8. Note that a maximum motion according to a viewing angle is determined for the motion function, and matching search exceeding the amount is not to be performed. Thus, it is possible to reduce calculation time, and prevent an impossible result.

Subsequently, the warping processing function 332 transforms a blood vessel shape in each of the first DSA-image data to match a blood vessel shape in the second DSA-image data (reference image data) by using the motion function (step S302). As illustrated in FIG. 7B, for example, the warping processing function 332 generates seven francs of transformation image data corresponding to t1 to t7 by subjecting each of the seven frames of the first DSA-image data corresponding to t1 to t7 to transformation by using the calculated motion function. In other words, the warping processing function 332 generates plural frames of third vessel-image data, whose observation direction is the second observation direction, by transforming more than one out of the plural frames of the first vessel-image data based on a blood vessel shape in at least one of the plural first vessel-image data and a blood vessel shape in one frame of second vessel-image data. The transformation image data corresponding to observation direction 2 is one example of the third vessel-image data, the third vessel image data corresponding to respective time phases of the plural frames of the first vessel image data.

The warping processing function 332 then transfers the transformation image data of plural time phases to the image memory 22 (step S303). For example, the warping processing function 332 transfers each of the seven frames of the transformation image data corresponding to t1 to t7 to the image memory 22.

The processing procedure illustrated in FIG. 6 is only one example, and is not necessarily limited to the illustrated example. For example, the processing of transferring the transformation image data (step S303) can be performed in parallel with the processing of generating the transformation image data (step S302).

Explanation returns to FIG. 3. When the transformation image data of plural time phases is generated, the parametric-image generating function 333 generates two pieces of parametric image data with different eyepoints (step S105). For example, the parametric-image generating function 333 generates first parametric-image data and second parametric-image data using the first vessel image data and the third vessel image data, respectively. The first parametric-image data is parametric image data corresponding to observation direction 1. Moreover, the second parametric-image data is parametric image data corresponding to observation direction 2. The parametric image data is one example of color image data.

For example, the parametric-image generating function 333 generates the first parametric-image data using seven frames of the first DSA-image data corresponding to t1 to t7. Furthermore, the parametric-image generating function 333 generates the second parametric-image data using the seven frames of the transformation image data corresponding to t1 to t2.

Specifically, the parametric-image generating function 333 identifies inflow time by using the seven frames of the first DSA-image data corresponding to t1 to t7. The inflow time is a parameter that is defined based on temporal changes in respective pixel values, assuming that the changes in pixel values at respective positions in DSA image data reflects changes in concentration of a contrast agent. As a method of identifying the inflow time, any identification method can be selected out of time-to-peak (TTP) and time-to-arrival (TTA). For example, TTS is a method of identifying time in which a change in pixel value with time reaches its maximum as the inflow time. TTA is a method of identifying time in which a change in pixel value with time reaches a predetermined value, or time in which a change in pixel value with time reaches a predetermine percentage of its maximum value as the inflow time.

When the inflow time is identified, the parametric-image generating function 333 generates first parametric-image data as a still image, by allocating colors to respective pixel positions according to the inflow time. The processing of generating the second parametric-image data is similar to the processing of generating the first parametric-image data except a point that inflow time is identified by using seven frames of transformation image data corresponding to t1 to t7, and therefore, explanation thereof is omitted. Alternatively, instead of generating seven frames of transformation image data, inflow time that is determined from the first DSA-image data can be assigned to inflow time that would be determined from the second DSA-image data using the motion function. In this case, the warping processing can be suppressed to be performed only once, and therefore, the processing time can be reduced. That is, the parametric-image generating function 333 generates the first parametric-image data by using the first DSA-image data of plural time phases. The warping processing function 332 subjects the first parametric-image data to the transformation processing using a blood vessel shape drawn in the second DSA-image data as the reference image data as a reference, and thereby generates the second parametric-image data corresponding to the second observation direction.

As described, the parametric-image generating function 333 generates the first parametric-image data and the second parametric-image data. In other words, the parametric-image generating function 333 generates first color-image data, whose observation direction is the first observation direction, and that reflects a flow of a contrast agent, by using more than one frame out of plural frames of the first vessel-image data, and generates second color-image data, whose observation direction is the second observation direction, and that reflects a flow of the contrast agent, by using more than one frame out of plural frames of the third vessel-image data. The first parametric-image data and the second parametric-image data are not limited to a still image, but can also be generated as an animation. For example, the parametric-image generating function 333 can generate the first parametric-image data and the second parametric-image data as an animation, by an animation display method in parametric imaging as described in Japanese Laid-Open Patent Publication No 2014-200339.

The display control function 334 then displays a stereoscopic image by using two pieces of parametric-image data with different eyepoints (step S106). For example, the display control function 334 displays a stereoscopic image on the display 40 by using the first parametric-image data and the second parametric-image data.

When the viewing angles are not in a left-right direction of a patient, rotation processing of the first parametric-image data and the second parametric-image data by using the affine transformation circuitry 25 is necessary at displaying the first parametric-image data and the second parametric-image data. The rotation processing is performed such that a projection direction of a rotation axis is vertical direction. For example, when rotating in the vertical direction, specifically, when the first observation angle is RAO30CRA0 and the second observation angle is RAO30CRA5, the first parametric-image data and the second parametric-image data are displayed in a 90-degree rotated manner to the right, or in a 90-degree rotated manner to the left. Furthermore, for example, when rotating from a patient lower right direction to a patient upper left direction, specifically, when the first observation angle is RAO2CRA2, and the second observation angle is LAO2 CAU2, the first parametric-image data and the second parametric-image data are displayed in a 45-degree rotated manner to the right, or a 135-degree rotated manner to the left. That is, the parametric-image generating function 333 acquires a rotation-axis projection image that is obtained by projecting as if a rotation axis in rotating from the first observation direction to the second observation direction is imaged from a focal position of the X-ray tube when imaging from each of the observation directions at a detector position of that time, and generates the first color-image data and the second color-image data so that this rotation-axis projection image is aligned the vertical direction.

Although the example in which parametric image data is rotated is explained herein, the FPD can be rotated to acquire similar parametric image instead of rotating the parametric image data. That is, the DSA-image generating function 331 acquires a rotation-axis projection image that is obtained by projecting as if a rotation axis in rotating from the first observation direction to the second observation direction is imaged from a focal position of the X-ray tube when imaging from each of the observation directions at a detector position of that time, and rotates the detector such that this rotation-axis projection image is aligned the vertical direction to generate the first contrast-image data, the first non-contrast-image data, the second contrast-image data, and the second non-contrast-image data.

As described above, in the X-ray diagnostic apparatus 1 according to the first embodiment, the DSA-image generating function 331 generates the first DSA-image data of plural time phases by subtracting the first mask-image data from each of plural frames of the first contrast-image data of plural time phases collected in a period from start of injection of a contrast agent. Moreover, the DSA-image generating function 331 generates one frame of the second DSA-image data by subtracting the second mask-image data from at least one frame of the second contrast-image data that is collected after collection of the first contrast-image data. The warping processing function 332 generates the transformation image data of plural time phases corresponding to the second observation direction by subjecting the first DSA-image data of plural time phases to the transformation processing based on a blood vessel shape drawn in the second DSA-image data as reference image data. The parametric-image generating function 333 generates the first parametric-image data by using the first DSA-image data of plural time phases, and generates the second parametric-image data by using the transformation image data of plural time phases or transforming the first parametric-image data.

That is, the X-ray diagnostic apparatus 1 according to the first embodiment performs the warping processing to generate, from time-series DSA image data of one observation direction, time-series DSA image data of another observation direction artificially. This enables the X-ray diagnostic apparatus 1 according to the first embodiment to provide a stereoscopic image in parametric imaging easily. For example, the X-ray diagnostic apparatus 1 can generate two pieces of parametric image data with different eyepoints with injection of a contrast agent performed only once and, therefore, can provide a stereoscopic image easily.

Second Embodiment

Although the case in which a part that moves rarely, such as an intracranial vessels, is a target part has been explained in the first embodiment above, embodiments are not limited thereto. For example, the X-ray diagnostic apparatus 1 can target a part having periodical motion, such as an abdomen vessels and a heart, also. Therefore, in a second embodiment, a case in which a part having periodical motion is a target part is explained.

The X-ray diagnostic apparatus 1 according to the second embodiment has a configuration similar to the X-ray diagnostic apparatus 1 illustrated in FIG. 1, and a part of processing performed by the DSA-image generating function 331, the warping processing function 332, and the parametric-image generating function 333 is different therefrom. Therefore, in the second embodiment, points that differ from the first embodiment are mainly explained, and explanation of the configuration that has been explained in the first embodiment and points having similar functions thereto is omitted.

Specifically, the DSA-image generating function 331 collects first mask image data of plural time phases and mask-image data of plural time phases to cover periodical motion of organs, and thereafter collects first contrast image data of plural time phases and second contrast-image data of plural time phases while injecting a contrast agent. Thereafter, first subtraction-image data of plural time phases and second subtraction-image data of plural time phases are generated. At this time, the first contrast-image data of plural time phases is subjected to the subtraction processing by using the most suitable image selected from among the first mask-image data of plural time phases. The most suitable image can be determined based on an electrocardiogram, a respiratory waveform, or the like, or the most suitable image can be identified by any method described in Japanese Laid-Open Patent Publication No. 2004-112469, Japanese Laid-Open Patent Publication No. 2005-198330, Japanese Laid-Open Patent Publication No. 2007-215925, and the like. Similarly, the second contrast-image data of plural time phases are subjected to the subtraction processing by using the most suitable image selected from among the second mask-image data of plural time phases.

The warping processing function 332 determines first reference-image data to be a reference out of the first subtraction-image data of plural time phases and second reference-image data to be a reference out of the second subtraction-image data of plural time phases as reference image data based on similarities between the first subtraction-image data of plural time phases and the second subtraction-image data of plural time phases. The warping processing function 332 subjects the first subtraction-image data of plural time phases to the transformation processing using a blood vessel shape that is drawn in the determined first reference-image data as a reference, and thereby generates first transformation image data of plural time phases corresponding to the first observation direction. Moreover, the warping processing function 332 subjects the second subtraction-image data of plural time phases to the transformation processing using a blood vessel shape that is drawn in the determined second reference-image data as a reference, and thereby generates second transformation-image data of plural time phases corresponding to the second observation direction.

The parametric-image generating function 333 generates first parametric-image data and first color-image data by using the first transformation-image data of plural time phases and generates second parametric-image data and second color-image data by using the second transformation-image data of plural time phases.

Although processing procedure of the X-ray diagnostic apparatus 1 according to the second embodiment is similar to the processing procedure illustrated in FIG. 3, respective processing at step S103 and S104 are different. In the following, the processing procedure of the X-ray diagnostic apparatus according to the second embodiment is explained.

Figure 9:
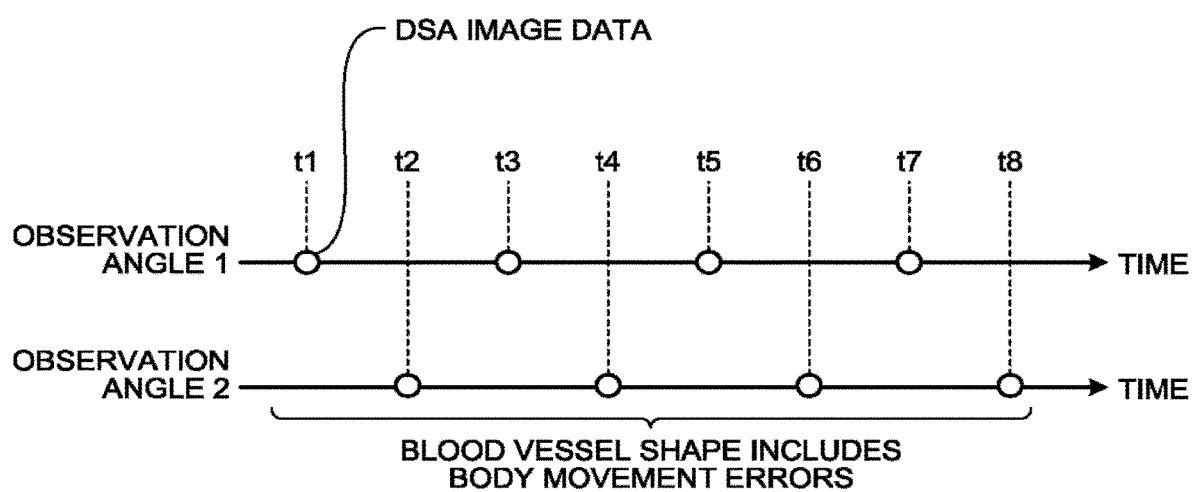
FIG. 9 is a diagram for explaining the DSA-image generation processing according to the second embodiment.

By using FIG. 8 and FIG. 9, DSA-image generation processing according to the second embodiment is explained. FIG. 8 is a flowchart illustrating the processing procedure of the DSA-image generation processing according to the second embodiment. FIG. 8 illustrates a processing procedure corresponding to the DSA-image generation processing at step S103 illustrated in FIG. 3. FIG. 9 is a diagram for explaining the DSA-image generation processing according to the second embodiment. In FIG. 9, a horizontal axis is for time. Moreover, a circle expresses DSA image data at that point.

As illustrated in FIG. 8, the DSA-image generating function 331 starts reciprocation of the C-arm 13 (step 401). This reciprocation can be movement traveling only between observation angle 1 and observation angle 2 alternately, and respective overruns for observation angle 1 and observation angle 2 can be considered also. That is, when observation angle 1 is RAO30CRA0 and observation angle 2 is RAO35CRA0, the reciprocation can take place between RAO25CRA0 and RAO40CRA0. When reciprocation takes place only between observation angle 1 and observation angle 2, time necessary for collecting images is reduced. On the other hand, when overruns are considered to be included, possibility that the C-arm 13 wobbles due to sudden stop can be decreased at the time of imaging.

Upon starting the reciprocation of the C-arm 13, the DSA-image generating function 331 collects first mask-image data and second mask-image data (step S402). The DSA-image generating function 331 repeats collection at step S402 until it is determined that collection has been performed for predetermined time (step S403: NO). Collection time (predetermined time) is determined based on period of a moving target part and imaging intervals. For example, the collection time is determined considering that sufficient frames of image data for a motion cycle are collected, and considering that image data of various states (phases) is collected. Specifically, in the case of respiratory movement (body movement), influence of the body movement disappears to be back to an original state (phase) in about 5 seconds. If the imaging interval is once in 0.5 seconds, 10 pieces of images can be collected before it returns to the original position. Therefore, in the case of respiratory movement, it is preferable that mask-image data of at least one cycle be collected. Moreover, in the case of heart beat, it returns to the original position (phase) in 1 second. In this case, if the imaging interval (frame rate) is set to 0.5 seconds, the heart at the same phase is to be imaged each time. Therefore, by adjusting (reducing) a rotation speed to set to 0.6 seconds. Thus, 5, 6 frames of images of different phases can be collected in about 3 seconds. The collection time can be, for example, registered in advance in the imaging program per target part, or can be specified each time by an operator.

When it is determined that collection has been performed for the predetermined time (step S403: YES), the DSA-image generating function 331 notifies to start injection of a contrast. agent (step S404). For example, the DSA-image generating function 331 displays an icon indicating injection start timing on the screen of the display 40, thereby notifying to start injection of the contrast agent. Not limited thereto, notification to start the injection can be done by sound output, or by displaying a count-down timer that indicates the injection start timing. Thus, the operator starts injection of the contrast agent using an injector. Or there may be cases in which injection of contrast agent is performed manually by physicians via syringes.

The DSA-image generating function 331 then collects the first contrast-image data and the second contrast-image data (step S405). The DSA-image generating function 331 repeats collection at step S405 until imaging is finished (step S406: NO). The collection time and the frame rate are similar to those in collection at step S402 and, therefore, explanation thereof is omitted. Furthermore, the collected first contrast-image data and second contrast-image data are displayed on the display 40 by the display control function 334 in substantially real time. For example, the operator finishes imaging when the contrast agent is still sufficiently present in a blood vessel (artery) and the target part is contrasted while observing the contrast image data displayed on the display 40, and transfers the collected contrast image data to the image memory 22. The transfer of the contrast image data can be performed in parallel with the collection.

When imaging is finished (step S406: YES), the DSA-image generating function 331 generates the first DSA-image data of plural time phases and the second DSA-image data of plural time phases (step S407). For example, the DSA-image generating function 331 generates the first DSA-image data by using the first contrast-image data and the first mask-image data that are collected at same observation angle 1. At this time, the DSA-image generating function 331 generates the first DSA-image data by using a combination of the first contrast-image data and the first mask-image data which have similar organ positions.

An example of a specific method is provided herein. First, an MinIP image is generated from the first mask-image data of plural time phases and the first contrast-image data of plural time phases, respectively. The MinIP image of the first mask-image data is an image in which minimum values acquired among the first mask-image data of plural time phases per pixel are applied as its pixel values. A MinIP image of the first contrast-image data is also calculated similarly, and subtraction image data is generated using the MinIP image of the first contrast-image data and the MinIP image of the first-mask image data. This subtraction image is an image expressing movement of the blood vessels. By performing threshold processing on this subtraction image data, a region in which the blood vessels move is extracted. Next, mask image data of a most suitable time phase is identified from among the first mask-image data of plural time phases for respective image data of the first contrast-image data of plural time phases. For example, plural frames of subtraction image data are generated from the first contrast-image data of a specific time phase and the first mask-image data of plural time phases. The square sum of the respective pixel values of this subtraction image data is calculated in a region other than the region in which the blood vessels move identified previously. The first mask-image data, the calculated smallest square sum of which is the smallest is the most suitable first mask-image data for the first contrast-image data of an intended time phase. By performing the same processing for the first contrast-image data of all time phases, the first DSA-image data is generated.

The DSA-image generating function 331 transfers the first DSA-image data of plural time phases and the second DSA-image data of plural time phases to the image memory 22 (step S408). The transfer of the first DSA-image data and the second DSA-image data can be performed in parallel with generation of the first DSA-image data of plural time phases and the second DSA-image data. In other words, the DSA-image generating function 331 serving as the vessel-image generating unit generates plural frames of time-series first vessel-image data, whose observation direction is the first observation direction, and generates plural frames of time-series second vessel-image data, whose observation direction is the second observation direction.

The DSA image data of respective time phases generated by the DSA-image generating function 331 has motion errors. For example, as illustrated in FIG. 9, in the DSA image data of respective time phases of t1, t2, t3, t4, t5, t6, t7, t8, motion artifacts (artifact caused by subtraction) due to motion are suppressed. However, position errors of blood vessels are not suppressed between the DSA-image data of t1 and the DSA image data of t3, and the position errors are included in a blood vessel shape drawn in the respective image data. Therefore, to reduce motion errors between time phases at an identical observation angle, following warping processing is performed.

Figure 10:
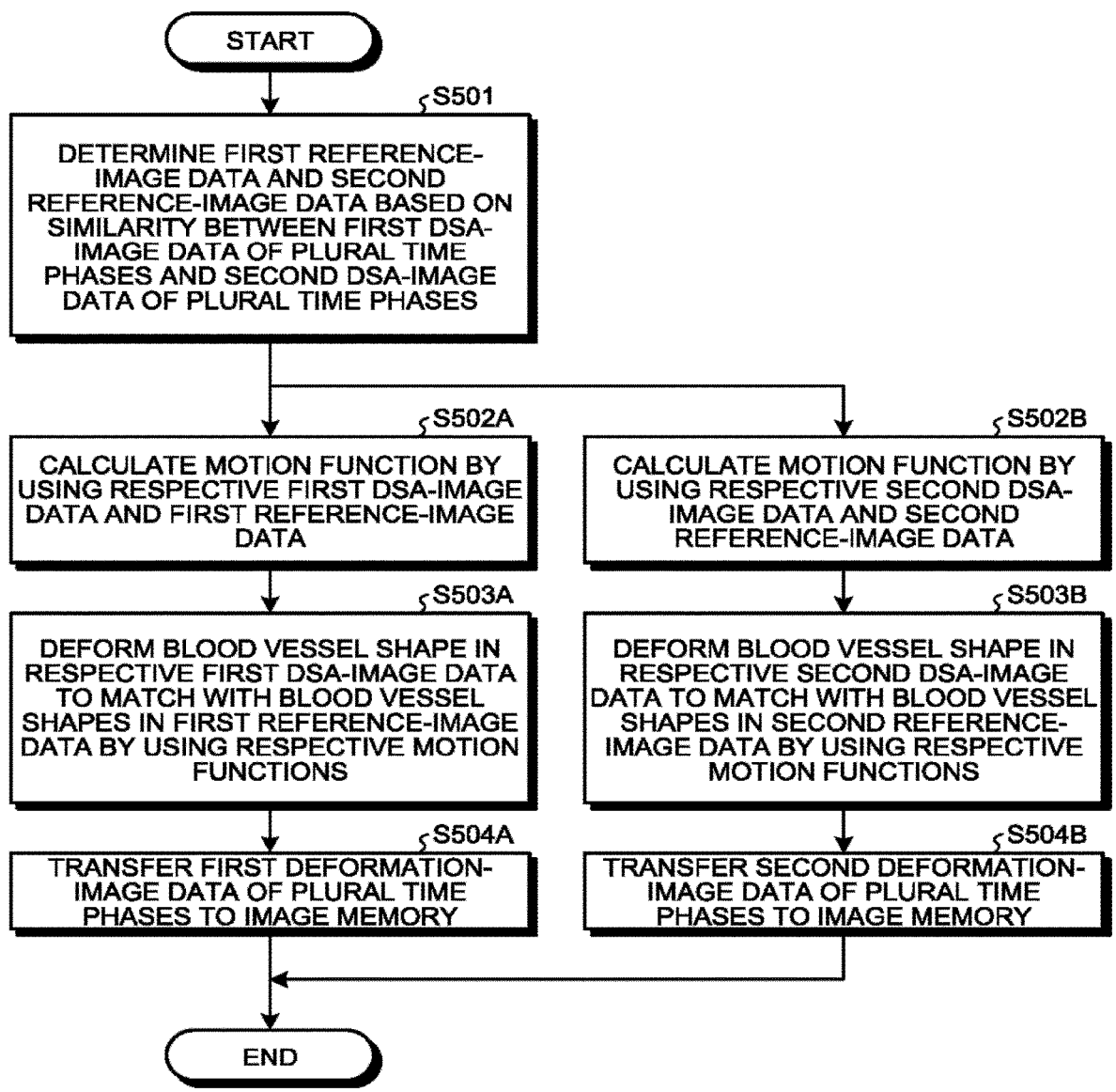
FIG. 10 is a flowchart illustrating a processing procedure of warping processing according to the second embodiment.
Figure 11A:
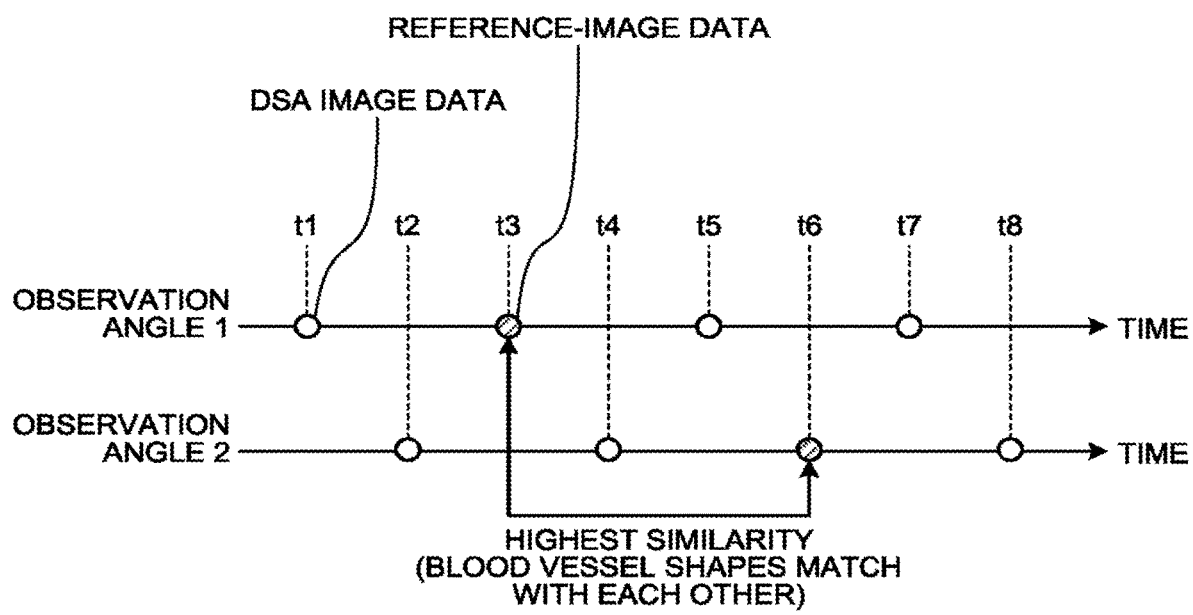
Figure 11B:
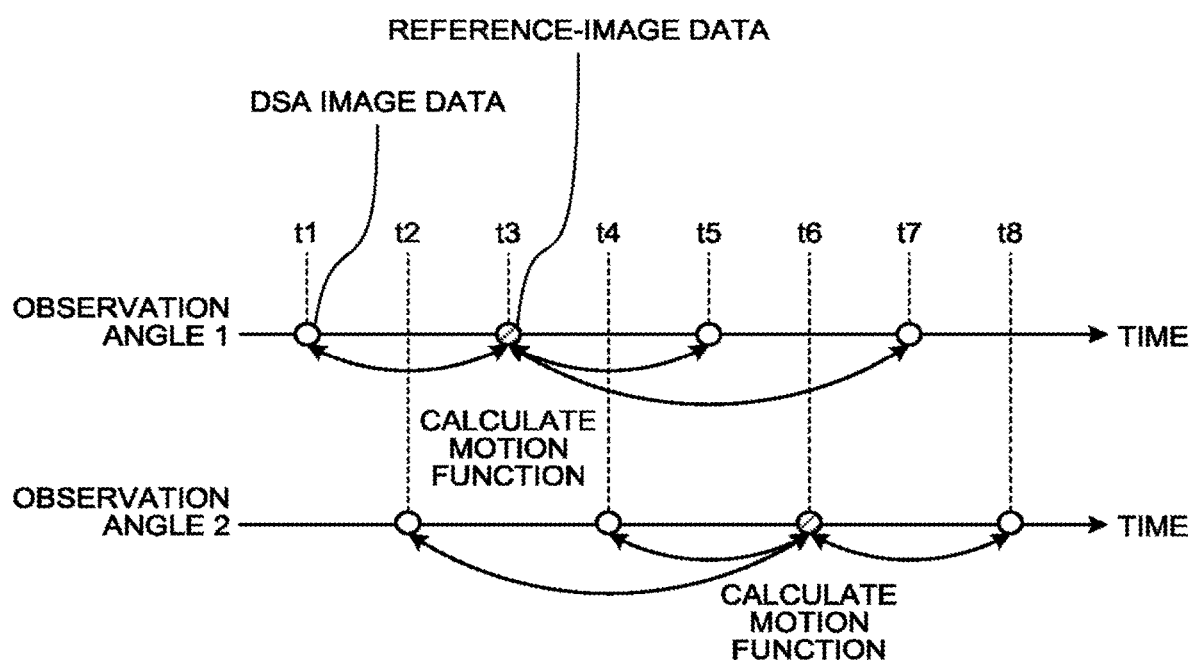

Warping processing according to the second embodiment is explained using FIG. 10, FIG. 11A, FIG. 11B, and FIG. 11C. FIG. 10 is a flowchart illustrating a processing procedure of the warping processing according to the second embodiment. FIG. 10 illustrates processing procedure corresponding the warping processing at step S103 illustrated in FIG. 3. FIG. 11A, FIG. 11B, and FIG. 11C are diagrams for explaining the warping processing according to the second embodiment. In FIG. 11A, FIG. 11B, and FIG. 11C, a horizontal axis is for time. Furthermore, in FIG. 11A, FIG. 11B, and FIG. 11C, a white circle expresses DSA image data at that point, and a block circle expresses transformation image data at that point.

As illustrated in FIG. 10 and FIG. 11A, the warping processing function 332 determines the first reference-image data and the second reference-image data based on similarities between the first DSA-image data of plural time phases and the second DSA-image data of plural time phases (step S501). Thus, the warping processing function 332 extracts a combination of the DSA image data in which the blood vessel shapes match with each other at observation angle 1 and observation angle 2.

Specifically, the warping processing function 332 calculates a similarity of the DSA image data between "t1" and "t2", a similarity of the DSA image data between "t1" and "t4", a similarity of the DSA image data between "t1" and "t6", and a similarity of the DSA image data between "t1" and "t8". Moreover, the warping processing function 332 calculates a similarity of the DSA image data between "t3" and "t2", a similarity of the DSA image data between "t3" and "t4", a similarity of the DSA image data between "t3" and "t6", and a similarity of the DSA image data between "t3" and "t8". Furthermore, the warping processing function 332 calculates a similarity of the DSA image data between "t5" and "t2", a similarity of the DSA image data between "t5" and "t4", a similarity of the DSA image data between "t5" and "t6", and a similarity of the DSA image data between "t5" and "t8". Moreover, the warping processing function 332 calculates a similarity of the DSA image data between "t7" and "t2", a similarity of the DSA image data between "t7" and "t4", a similarity of the DSA image data between "t7" and "t6", and a similarity of the DSA image data between "t7" and "t8".

Subsequently, the warping processing function 332 compares the calculated similarities with each other. For example, when the similarity of the DSA image data between "t3" and "t6" is highest, it can be considered that blood vessel shapes drawn in these frames of the image data match. In this case, the warping processing function 332 determines the first DSA-image data of t3 as the first reference-image data, and the second DSA-image data as the second reference-image data.

Subsequently, the warping processing function 332 respectively calculates motion functions by using the respective frames of the first DSA-image data and the first reference-image data (step S502A) as illustrated in FIG. 11B. Specifically, the warping processing function 332 calculates a motion function between "t1" and "t3", a motion function between "t3" and "t5", and a on function between "t3" and The warping processing function 332 transforms a blood vessel shape in the respective first DSA-image data so as to match with a blood vessel shape in the first reference-image data by using the respective motion functions (step S503A) Specifically, the warping processing function 332 transforms the first DSA-image data of "t1" by using the motion function between "t1" and "t3" to generate transformation image data of "t1". Moreover, the warping processing function 332 transforms the first DSA-image data of "t5" by using the motion function between "t3" and "t5" to generate transformation image data of "t5". Furthermore, the warping processing function 332 transforms the first DSA-image data of "t7" by using the motion function between "t3" and "t7" to generate transformation image data of "t7".

As described, the warping processing function 332 generates the first transformation-image data of plural time phases. The first transformation-image data is transformation image data corresponding to observation direction 1. Thus, blood vessel shapes drawn in the respective DSA-image data of t1, t3, t5, and t7 at observation angle 1 match with each other. In other words, the warping processing function 332 serving as an image processing unit generates plural frames of time-series third vessel-image data, whose observation direction is the first observation direction by performing transformation using at least one frame out of plural frames of first vessel-image data as a reference, the transformation of other frames of image data out of the plural frames of the first vessel-image data. That is, the first DSA-image data of t3, and the first transformation image-data of t1, t5, and t7 are one example of plural frames of the time-series third vessel-image data.

The warping processing function 332 then transfers the third vessel-image data of plural time phases to the image memory 2 (step S504A). The transfer of the third vessel-image data can be performed in parallel with generation of the third vessel-image data.

At step S502B to step S504B, the warping processing function 332 serving as the image processing unit generates plural frames of time-series fourth vessel-image data, whose observation direction is the second observation direction by transformation using at least one frame out of plural frames of second vessel-image data as a reference, the transformation of other frames of image data out of the plural frames of the second vessel-image data. That is, the second DSA-image data of t6, and the second transformation image-data of t2, t4, and t8 are one example of plural frames of the time-series fourth vessel-image data. The respective processing at step S502S to step S504S is the same as the respective processing at step S502A to step S504A except a point that it is processing for image data corresponding observation angle 2 and, therefore, explanation thereof is omitted.

As described, the warping processing function 332 matches blood vessel shapes drawn in the respective frames of the DSA-image data (transformation image data) of t1 to t8.

The parametric-image generating function 333 generates two pieces of parametric image data with different eyepoints by using the respective pieces of the DSA image data (transformation image data) of t1 to t8. For example, the parametric-image generating function 333 generates first parametric-image data by using the third vessel-image data (first transformation-image data) of respective time phases of t1, t3, t5, and t7. Moreover, the parametric-image generating function 333 generates second parametric-image data by using the fourth vessel-image data (second transformation-image data) of respective time phases of t2, t4, t6, and t8. In other words, the parametric-image generating function 333 serving as the color-image generating unit generates first color-image data, whose observation direction is the first observation direction and in which a flow of a contrast agent is reflected, based on plural frames of the third vessel-image data. Furthermore, the parametric-image generating function 333 generates second color-image data, whose observation direction is the second observation direction and in which the flow of the contrast agent is reflected, based on plural frames fourth vessel-image data.

As described, the X ay diagnostic apparatus 1 according to the second embodiment performs the warping processing to match blood vessel shapes different at respective observation angles artificially. Thus, the X-ray diagnostic apparatus 1 according to the second embodiment can generate two pieces of parametric image data with different eyepoints with injection of a contrast agent performed only once even when the target part is a part having periodical motion and, therefore, can provide a stereoscopic image easily.

Although the second embodiment has been explained using motion having periodicity as an example, embodiments are not limited thereto. For example, the X-ray diagnostic apparatus 1 according to the second embodiment can provide a stereoscopic image of a part that is affected by body movement without periodicity by collecting sufficient number of frames of contrast image data or mask image data.

Modification of Second Embodiment

Moreover, in the second embodiment, blood vessel shapes in the respective first DSA-image data and the respective second DSA-image data are transformed to match with a blood vessel shape in the first reference-image data and second reference-image data, respectively. However, the X-ray diagnostic apparatus 1 according to the second embodiment can additionally transform blood vessel shapes in the respective first DSA-image data and the respective second DSA-image data to blood vessel shapes in the second reference-image data and the first reference-image data, respectively. While the warping processing takes twice as much time by this processing, the time resolution can be improved in generating two pieces of parametric image data.

Figure 12:
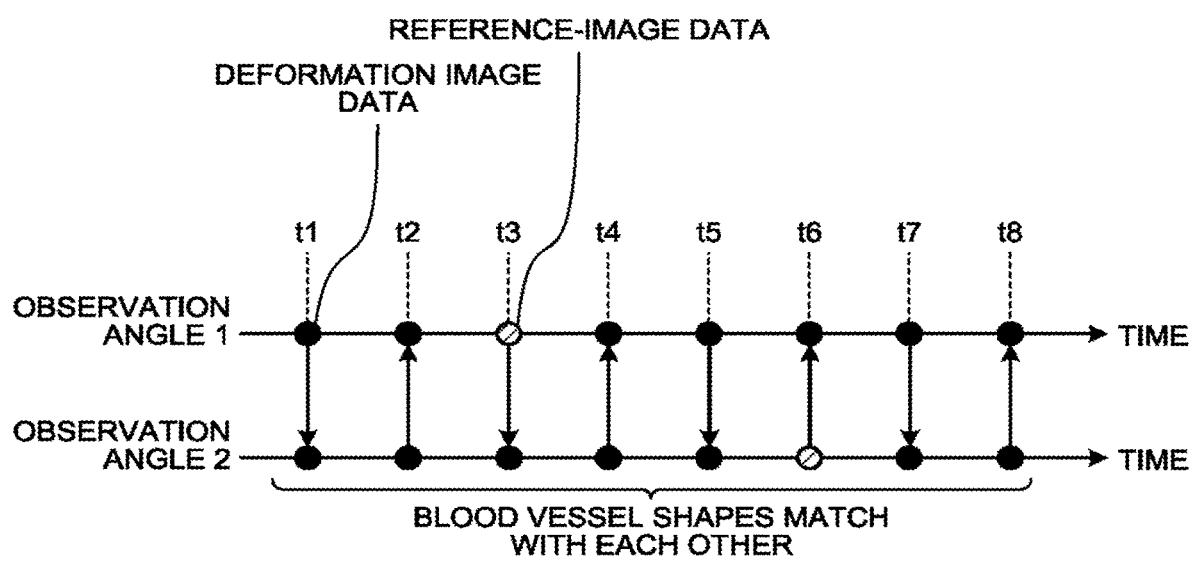
FIG. 12 is a diagram for explaining processing of an X-ray diagnostic apparatus according to a modification of the second embodiment.

Processing performed by the X-ray diagnostic apparatus according to a modification of the second embodiment is explained using FIG. 12. FIG. 12 is a diagram for explaining processing performed by the X-ray diagnostic apparatus according to the modification of the second embodiment. The X-ray diagnostic apparatus according to the modification of the second embodiment performs processing explained in FIG. 12 in addition to the processing explained in FIG. 11A to FIG. 11C.

As illustrated in FIG. 12, in the X-ray diagnostic apparatus 1, the warping processing function 332 calculates respective motion functions using the respective second DSA-image data and the first reference-image data. Specifically, the warping processing function 332 calculates a motion function between "t2" and "t3", a motion function between "t3" and "t4", a motion function between "t3" and "t6", and a motion function between "t3" and "t8".

The warping processing function 332 then transforms blood vessel shapes in the respective second DSA-image data to match with a blood vessel shape in the first reference-image data using the respective motion functions. Specifically, the warping processing function 332 generates transformation image data of "t2" corresponding to observation angle 1 by transforming the second DSA-image data of "t2" using the motion function between "t2" and "t3". Moreover, the warping processing function 332 generates transformation image data of "t4" corresponding to observation angle 1 by transforming the second DSA-image data of "t4" using the motion function between "t3" and "t4". Furthermore, the warping processing function 332 generates transformation image data of "t6" corresponding to observation angle 1 by transforming the second DSA-image data of "t6" using the motion function between "t3" and "t6". Moreover, the warping processing function 332 generates transformation image data of "t8" corresponding to observation angle 1 by transforming the second DSA-image data of "t8" using the motion function between "t3" and "t8". Thus, the warping processing function 332 can generate image data (DSA image data or transformation image data) corresponding to observation angle 1 for each of t1, t2, t3, t4, t5, t6, t7, and t8.

Similarly, the warping processing function 332 generates DSA image data corresponding to observation angle 2. That is, the warping processing function 332 calculates motion functions using the respective first DSA-image data and the second reference-image data. The warping processing function 332 then transforms blood vessel shapes in the respective first DSA-image data to match with a blood vessel shape in the second reference-image data using the respective motion functions. Thus, the warping processing function 332 can generate image data corresponding to observation angle 2 for each of t1, t2, t3, t4, t5, t6, t7, and t8.

That is, the warping processing function 332 generates the first transformation-image data of plural time phases corresponding to the first observation direction by subjecting the first subtraction-image data and the second subtraction-image data of plural time phases to transformation processing based on a blood vessel shape drawn in the determined first reference-image data. Moreover, the warping processing function 332 generates the second transformation-image data corresponding to the second observation direction by subjecting the first subtraction-image data and the second subtraction-image data of plural phases to transformation processing based on a blood vessel shape drawn in the determined second reference-image data.

As described, the X-ray diagnostic apparatus 1 according to the modification of the second embodiment can improve the time resolution. For example, in FIG. 11A to FIG. 11C, the case in which image data (DSA image data or transformation image data) of four time phases are generated in each of the observation directions have been explained. The X-ray diagnostic apparatus 1 according to the modification of the second embodiment performs processing explained in FIG. 12 in addition to the processing explained in FIG. 11A to FIG. 11C, and thereby generates image data of eight time phases in each of the observation directions. Therefore, the X-ray diagnostic apparatus 1 according to the modification of the second embodiment can improve the time resolution.

Third Embodiment

In a third embodiment, a case in which X-ray image data of observation angle 1 and observation angle 2 by vibration of the C-arm 13 is explained.

The X-ray diagnostic apparatus 1 according to the third embodiment has the same configuration as the X-ray diagnostic apparatus 1 illustrated in FIG. 1, but differs therefrom in a point that an acceleration sensor is further included, and in a part of processing of the DSA-image generating function 331, the warping processing function 332, and the parametric-image generating function 333. Therefore, in the third embodiment, points that differ from e first embodiment are mainly explained, and explanation about points having the same functions as those in the configuration explained in the first embodiment is omitted.

Specifically, the DSA-image generating function 331 generates the first subtraction-image data of plural time phases and the second subtraction-image data of plural time phases by using the first contrast-image data of plural time phases and the second contrast-image data of plural time phases that are collected while the first observation direction and the second observation direction are switched therebetween by vibration of the C-arm 13 that supports the X-ray tube 11 and the X-ray detector 12.

The warping processing function 332 determines the first reference-image data to be a reference out of the first subtraction-image data of plural time phases, and the second reference-image data to be a reference out of the second subtraction-image data of plural time phases. Subsequently, the warping processing function 32 subjects the first subtraction-image data of plural time phases to transformation processing based on a blood vessel shape that is drawn in the determined first reference-image data, and thereby generates the third vessel-image data of plural time phases corresponding to the first observation direction. Moreover, the warping processing function 332 subjects the second subtraction-image data of plural time phases to transformation processing based on a blood vessel shape that is drawn in the determined fourth vessel-image data, and thereby generates the second transformation-image data of plural time phases corresponding to the second observation direction.

Figure 13A:
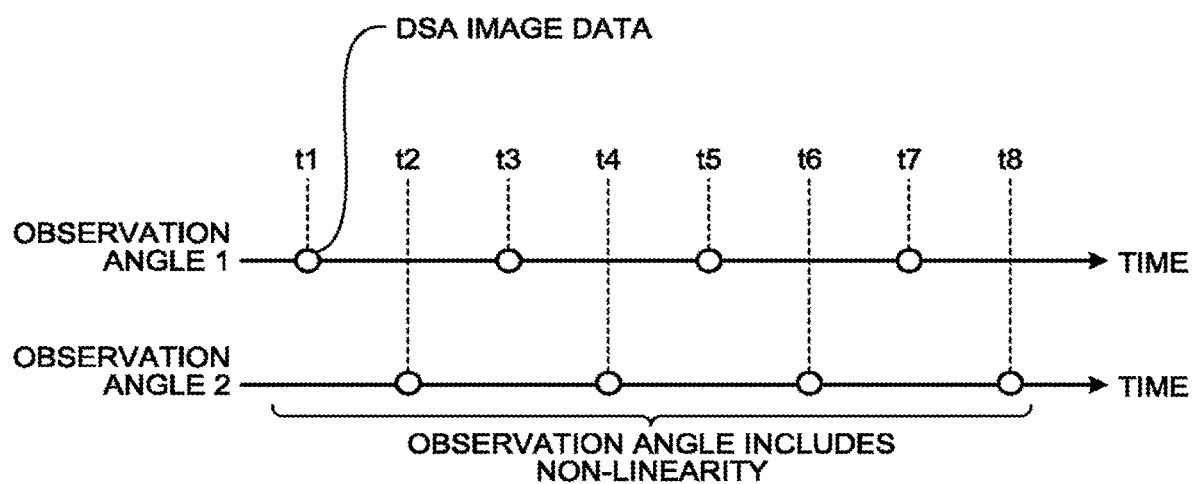
FIG. 13A to FIG. 13D are diagrams for explaining processing of an X-ray diagnostic apparatus according to a third embodiment.
Figure 13B:
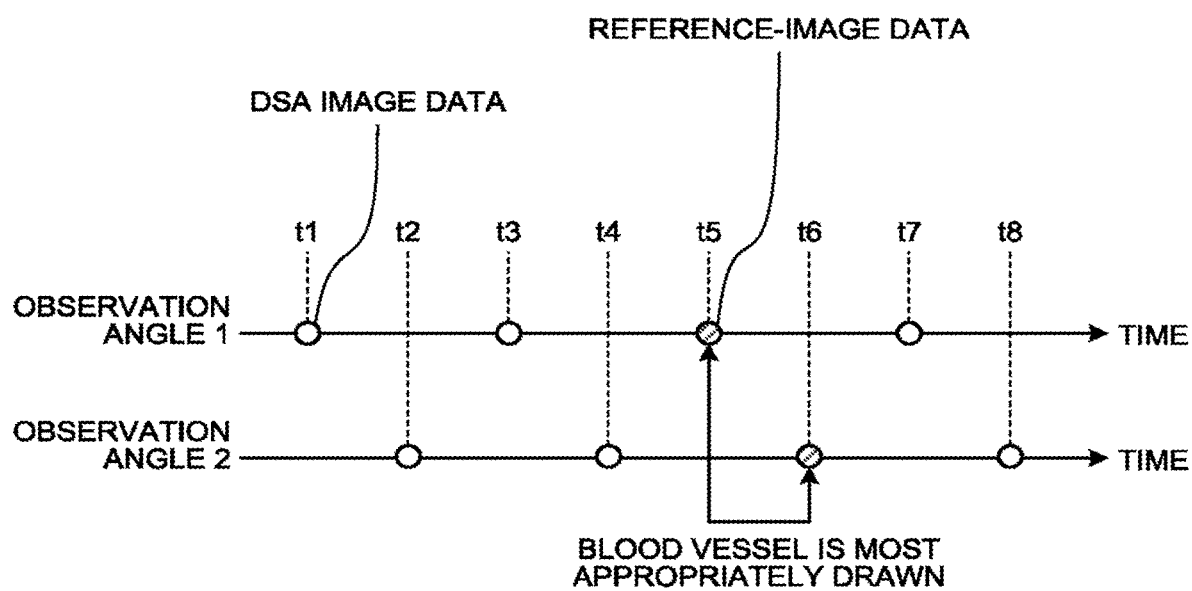
Figure 13C:
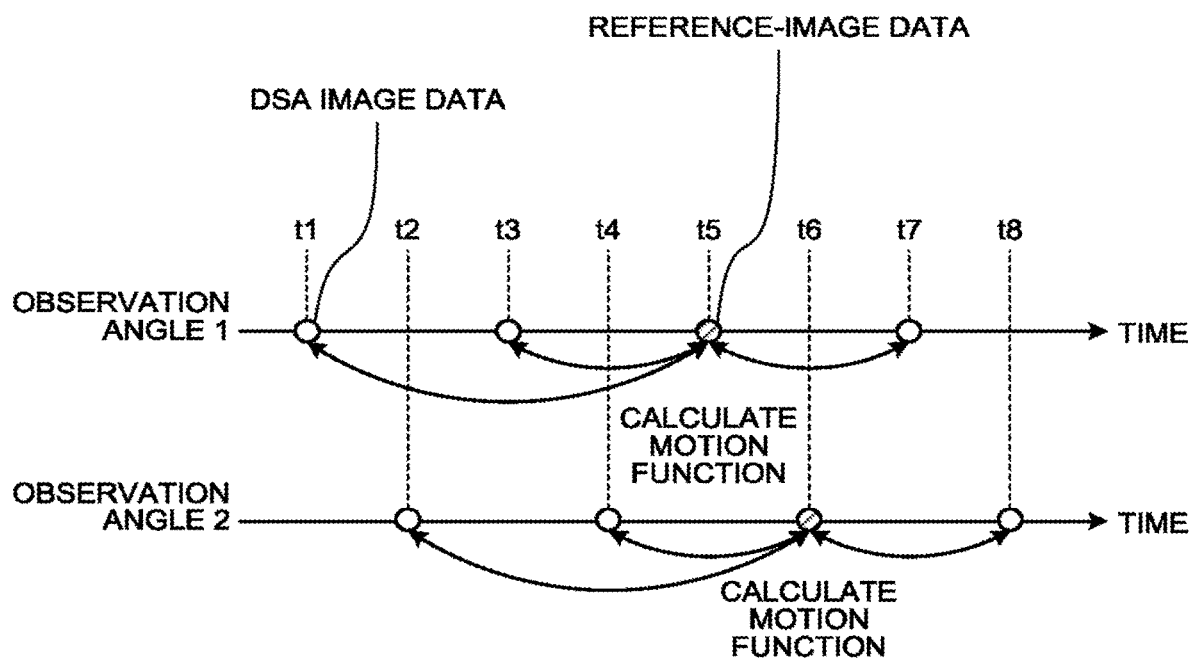
Figure 13D:
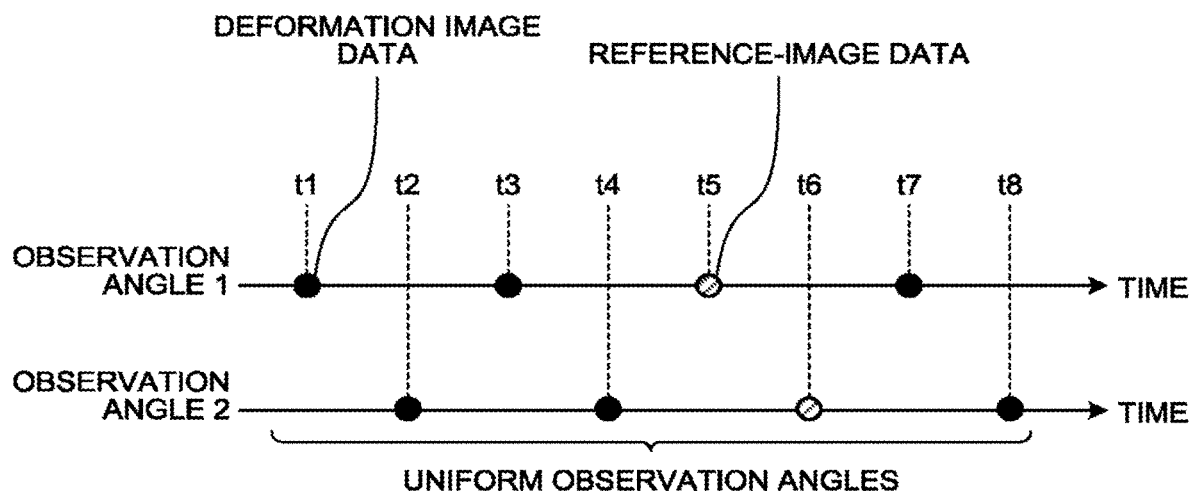

The parametric-image generating function 333 generates the first color-image data by using the first transformation-image data of plural time phases, and generates the second color-image data by using the second transformation-image data of plural time phases The processing performed by the X-ray diagnostic apparatus according to the third embodiment is explained using FIG. 13A, FIG. 13D, FIG. 13C, and FIG. 13D. FIG. 13A, FIG. 13B, FIG. 13C, and FIG. 13D are diagrams for explaining the processing of the X-ray diagnostic apparatus 1 according to the third embodiment. In FIG. 13A, FIG. 13B, FIG. 13C, and FIG. 13D, a horizontal axis is for time, a white circle expresses DSA image data at that point, and a black circuit expresses transformation image data at that point.

As illustrated in FIG. 13A, the DSA-image generating function 331 collects X-ray image data of observation angle 1 and observation angle 2 alternately by vibration of the C-arm 13. For example, the DSA-image generating function 331 drives a motor for rotation while applying brakes to rotation of the C-arm 13, thereby vibrating the C-arm 13. Alternatively, the DSA-image generating function 331 suddenly stops rotation while rotating the C-arm 13 at high speed, thereby vibrating the C-arm 13.

When vibration occurs, the acceleration sensor provided to the C-arm 13 detects peaks and valleys of the vibration. For example, the acceleration sensor identifies positions at which an acceleration of the C-arm 13 is 0 (or minimum) as a peak and a valley. The DSA-image generating function 331 collects mask-image data at the identified peaks and valleys. In other words, the imaging control circuitry 27 acquires plural pieces of time-series first contrast-image data and time-series second contrast-image data by performing imaging while repeatedly changing the observation direction of the imaging mechanism between the first observation direction and the second observation direction. Specifically, the imaging control circuitry 27 performs imaging, repeatedly changing the observation direction of the imaging mechanism between the first observation direction and the second observation direction by vibrating the imaging mechanism.

The method of detecting peaks and valleys of vibration is not limited to that by the acceleration sensor. For example, an angle sensor or a position sensor can be used to detect peaks and valleys of vibration. For example, the angle sensor or the position sensor measures an amount of change at short intervals, such as 0.1 send interval, and determines points at which the measured amount of change is equal to or smaller than a certain amount as substantial standstills peak and valley of vibration). Upon completion of collection of the mask image data, the DSA-image generating function 331 notifies to start injection of a contrast agent. Thus, an operator starts injection of the contract agent. The DSA-image generating function 331 then collects contrast image data while vibration of the C-arm 13 continues. The operator finishes imaging when the contrast agent is still sufficiently present in a blood vessel (artery) and the target part is contrasted while observing the contrast image data displayed on the display 40, and transfers the collected contrast image data to the image memory 22. The transfer of the contrast image data can he performed in parallel with the collection.

When imaging is finished, the DSA-image generating function 331 generates the first DSA-image data by using the first contrast-image data and the first mask-image data that are collected at same observation angle 1. At this time, the DSA-image generating function 331 generates the first DSA-image data by using a combination of the first contrast-image data having less errors due to motion and the first mask-image data. As a method of identifying a combination of the first contrast-image data having less errors due to motion and the first mask-image data has been explained in the second embodiment, explanation thereof is omitted herein. Moreover, after identifying the first mask-image data to be matched with the first contrast-image data, to further reduce artifact, the first DSA-image data can be generated, comparing the first mask-image data to be matched, with the first contrast-image data, calculating the motion function (motion vector), and transforming the first mask-image to be matched. Thus, parametric image data less affected by artifact can be generated, thereby producing an advantage that observation is facilitated. The second DSA-image data is also generated similarly. In other words, the DSA-image generating function 331 serving as the vessel-image generating unit generates plural frames of the first vessel-image data based on plural frames of the first contrast-image data, and generates plural frames of vessel-image data based on plural frames of the second contrast-image data. The DSA-image generating function 331 generates plural frames of the first vessel-image data by subtracting non-contrast image data corresponding to the first contrast-image data from each of the plural frames of the first contrast-image data, and generates plural frames of the second vessel-image data by subtracting non-contrast image data corresponding to the second-contrast image data from each of the plural frames of the second contrast-image data.

As illustrated in FIG. 13, the DSA-image generating function 331 collects the first DSA-image data at respective time phases of t1, t3, t5, and t7, and collects the second DSA-image data at respective time phases of t2, t4, t6, and t8. As the DSA image data is collected during the C-arm 13 is vibrating, a little change in observation angle can cause a transformation of a blood vessel shape due to influence of attenuation of vibration, or the like. In other words, the DSA-image generating function 331 serving as the vessel-image generating unit generates plural frames of the second Bessel-image data in time-series.

As illustrated in FIG. 13B, the DSA-image generating function 331 determines the first reference-image data and the second reference-image data. For example, the operator selects a frame in which an artery is drawn in a most appropriate manner from among the first DSA-image data, and a frame in which an artery is drawn in a most appropriate manner from among the second DSA-image data. The DSA-image generating function 331 determines image data of the frames selected by the operator as the first reference-image data and the second reference-image data. The first reference-image data and the second reference-image data can be determined automatically to image data that is estimated to have less blurriness by checking the intensity of a high frequency component by the Fourier transform of image data.

As illustrated in FIG. 13C, the warping processing function 332 calculates respective motion functions by using the respective first DSA-image data and the first reference-image data. Specifically, the warping processing function 332 calculates a motion function between "t1" and "t5", a motion function between "t3" and "t5", and a motion function between "t5" and "t7".

As illustrated in FIG. 13G, the warping processing function 332 transforms blood vessel shapes in the respective first DSA-image data to match with a blood vessel shape in the first reference-image data by using the respective motion functions. Specifically, the warping processing function 332 transforms the first DSA-image data of "t1" by using the motion function between "t1" and "t5", thereby generating the transformation image data of "t1". Moreover, the warping processing function 332 transforms the first DSA-image data of "t3" by using the motion function between "t3" and "t5", thereby generating the transformation image data of "t3". Furthermore, the warping processing function 332 transforms the first DSA-image data of "t7" by using the motion function between "t5" and "t7", thereby generating the transformation image data of "t7".

As described, the warping processing function 332 generates the first transformation-image data of plural time phases. Thus, observation angles drawn in the respective USA image data of t1, t3, t5, and t7 at observation angle 1 become uniform. The second transformation-image data is also generated by processing similar to that of the first transformation-image data. In other words, the warping processing function 332 serving as the image processing unit generates the third vessel-image data by subjecting plural frames of the first vessel-image data to transformation processing, and generates fourth vessel-image data by subjecting plural frames of the second vessel-image data to transformation processing.

The warping processing function 332 then transfers the first transformation-image data of plural time phases and the second transformation-image data of plural time phases to the image memory 22. The transfer of the transformation image data can be performed in parallel with generation of the transformation image data.

The parametric-image generating function 333 generates the first parametric-image data by using the third vessel-image data (first transformation-image data) of respective time phases of t1, t3, t5, and t7. Furthermore, the parametric-image generating function 333 generates the second parametric-image data by using the fourth vessel-image data (second transformation-image data) of respective time phases of t2, t4, t6, and t8.

Modification of Third Embodiment

Moreover, in the third embodiment, blood vessel shapes in the respective first DSA-image data and second DSA-image data can be transformed to blood vessel shapes in the first reference-image data and the second reference-image data similarly to modification of the second embodiment. While the warping processing takes twice as much time by this processing, the time resolution can be improved in generating two pieces of parametric image data.

Figure 14:
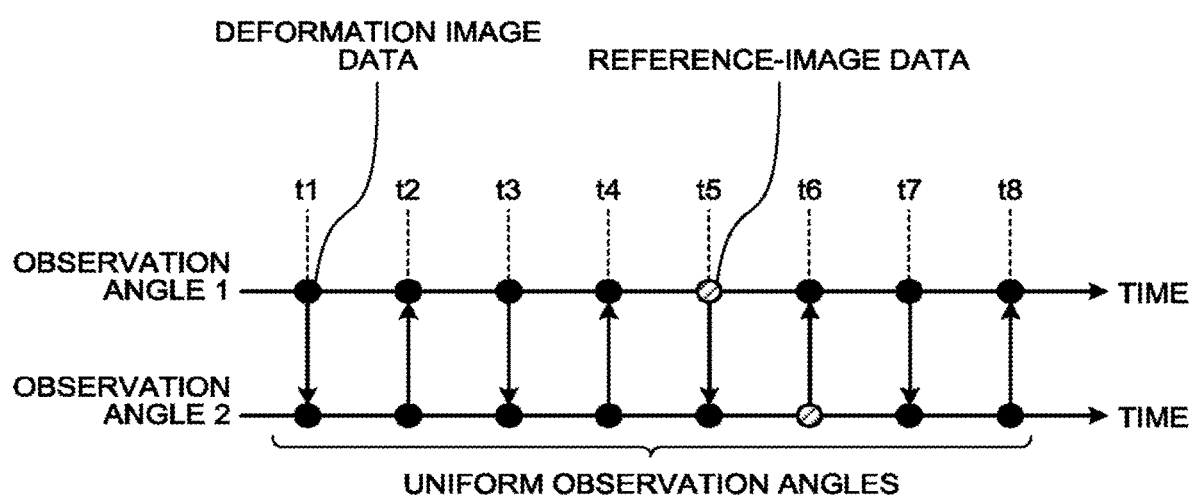
FIG. 14 is a diagram for explaining processing of the X-ray-diagnostic apparatus according to a modification of the third embodiment.

Processing performed by the X-ray diagnostic apparatus 1 according to a modification of the third embodiment is explained using FIG. 14. FIG. 14 is a diagram for explaining the processing performed by the X-ray-diagnostic apparatus 1 according to the modification of the third embodiment. The X-ray diagnostic apparatus 1 according to the modification of the third embodiment performs processing explained in FIG. 14 in addition to the processing explained in FIG. 13A to FIG. 13D.

As illustrated in FIG. 14, in the X-ray diagnostic apparatus 1, the warping processing function 332 calculates respective motion functions by using the respective second DSA-image data and the first reference-image data. Specifically, the warping processing function 332 calculates a motion function between "t2" and "t5", a motion function between "t4" and "t5", a motion function between "t5" and "t6", and a motion function between "t3" and "t8".

The warping processing function 332 then transforms blood vessel shapes in the respective second DSA-image data to match with a blood vessel shape in the first reference-image data using the respective motion functions. Specifically, the warping processing function 332 generates transformation image data of "t2" corresponding to observation angle 1 by transforming the second DSA-image data of "t2" using the motion function between "t2" and "t5". Moreover, the warping processing function 332 generates transformation image data of "t4" corresponding to observation angle 1 by transforming the second DSA-image data of "t4" using the motion function between "t4" and "t5". Furthermore, the warping processing function 332 generates transformation image data of "t6" corresponding to observation angle 1 by transforming the second DSA-image data of "t6" using the motion function between "t5" and "t6". Moreover, the warping processing function 332 generates transformation image data of "t4" corresponding to observation angle 1 by transforming the second DSA-image data of "t8" using the motion function between "t5" and "t8". Thus, the warping processing function 332 can generate the third vessel-image data (DSA image data or transformation image data) corresponding to observation angle 1 for each of t1, t2, t3, t4, t5, t6, t7, and t8. The transformation image data corresponding to observation angle 2 of "t2", "t4", and "t8" is one example of the fourth vessel-image data. That is, the warping processing function 332 serving as the image processing unit generates the third-vessel image data, whose observation direction is the first observation direction, by transforming more than one frame out of the plural frames of the first vessel-image data based on a blood vessel shape in one out of plural frames of the first vessel-image data and a blood vessel shape in at least one out of plural frames of the second vessel-image data, the fourth-vessel image data corresponding to respective time phases of the plural frames of the first vessel image data.

Similarly, the warping processing function 332 generates the fourth vessel-image data corresponding to observation angle 2. That is, the warping processing function 332 calculates motion functions between the respective first DSA-image data and the second reference-image data, and between the respective second DSA-image data and the second reference-image data. The warping processing function 332 then transforms blood vessel shapes in the respective first DSA-image data and second DSA-image data to match with a blood vessel shape in the second reference-image data and the first reference-image data using the respective motion functions, respectively. Thus, the warping processing function 332 can generate image data corresponding to observation angle 2 for each of t1, t2, t3, t4, t5, t6, t7, and t8. The transformation image data corresponding to observation angle 2 of "t1", "t3", "t5", and "t7" is one example of the third vessel-image data. That is, the warping processing function 332 serving as the image processing unit generates plural frames of the third vessel-image data, whose observation direction is the first observation direction, by transforming more than one frame out of the plural frames of the first vessel-image data based on a blood vessel shape in at least one out of the plural frames of the first vessel-image data and a blood vessel shape in at least one out of the plural frames of the second vessel-image data, the third vessel-image data corresponding to the respective time phases of plural frames of the first vessel-image data.

That is, the warping processing function 332 generates the first transformation-image data of plural time phases corresponding to the first observation direction by subjecting the first subtraction-image data and the second subtraction-image data of plural time phases to transformation processing based on a blood vessel shape drawn in the determined first reference-image data. Moreover, the warping processing function 332 generates the second transformation-image data of plural time phases corresponding to the second observation direction by subjecting the first subtraction-image data and the second subtraction-image data of plural phases to transformation processing based on a blood vessel shape drawn in the determined second reference-image data.

As described, the X-ray diagnostic apparatus 1 according to the modification of the third embodiment can improve the time resolution. For example, in FIG. 11A to FIG. 11C, the case in which image data of four time phases in each of the observation directions is generated has been explained. The X-ray diagnostic apparatus 1 according to the modification of the second embodiment performs processing explained in FIG. 12 in addition to the processing explained in FIG. 11A to FIG. 11C, and thereby generates image data of eight time phases in each of the observation directions. Therefore, the X-ray diagnostic apparatus 1 according to the modification of the second embodiment can improve the time resolution.

That is, the parametric age generating function 333 serving as the color-image generating unit generates the first color-image data based on more than one out of plural frames of the third vessel-image data. Moreover, the parametric-image generating function 333 generates the second color-image data based on more than one out of plural frames of the fourth vessel-image data.

Furthermore, in the third embodiment, the warping processing can be omitted when imaging time is short enough to finish imaging before oscillation changes. This has an advantage that processing time can be significantly shortened.

As described, the X-ray diagnostic apparatus 1 according to the third embodiment can provide a stereoscopic image easily even when X-ray image data of observation angle 1 and observation angle 2 is collected by vibration of the C-arm 13.

Other Embodiments

Other than the embodiments described above, various different forms can be applied.
Vessel Image Data Although the case in which parametric imaging is performed using DSA image data has been explained in the above embodiments, it is not limited thereto. For example, the embodiments described above are applicable to a case in which parametric imaging is performed using vessel image data. The DSA image data is one example of the vessel image data.

For example, the processing circuitry 33 performs vessel-image generating function instead of the DSA-image generating function 331. The vessel-image generating function generates vessel image data by either one of two methods below. The vessel-image generating function is one example of the vessel-image generating unit.

A first method is a method of generating vessel image data by machine learning. In machine learning, learned model to acquire an input to an output is generated by supervised learning using data for learning in which the contrast image data is an input and the USA image data is an output. This learned model generates, when contrast image data is input, vessel image data from which background components (bony tissues, soft tissues, and the like) other than blood vessels (contrast agent) are removed from the contrast image data. When the first method is used, the vessel-image generating function has the learned model described above. That is, the vessel-image generating function generates the first vessel-image data corresponding to observation angle 1 by inputting the first contrast-image data corresponding to observation angle 1 to the learned model. Moreover, the vessel-image generating function generates the second vessel-image data corresponding to observation angle 2 by inputting the second contrast-image data corresponding to observation angle 2 to the learned model. The generated first vessel-image data and second vessel-image data can be used instead of the first DSA-image data and the second DSA-image data in the embodiments described above.

A second method is a method in which vessel image data is generated by extracting high frequency components from contrast image data. In this case, the vessel-image generating function generates low-frequency-component image data that is obtained by extracting low frequency components (soft tissues, and the like) in the contrast image data by applying a lowpass filter (filtering processing) to the contrast image data. The vessel-image generating function generates high-frequency-component image data in which high frequency components (contrast agent components) of the contrast image data are extracted, by subtracting the low-frequency-component image data subtraction processing) from the original contrast image data. The high-frequency-component image data can be used as the vessel-image data. That is, the vessel-image generating function generates the first vessel-image data corresponding to observation angle 1 by subjection the first contrast-image data corresponding to observation angle 1 to the filtering processing and the subtraction processing described above. Furthermore, the vessel-image generating function generates the second vessel-image data corresponding to observation angle 2 by subjecting the second contrast-image data corresponding to observation angle 2 to the filtering processing and the subtraction processing described above. The generated first vessel-image data and second vessel-image data can be used instead of the first DSA-image data and the second DSA-image data in the embodiments described above.

Moreover, the respective components of the respective devices illustrated are of functional concept, and it is not necessarily required to be configured physically as illustrated. That is, specific forms of distribution and integration of the respective devices are not limited to the ones illustrated, and all or a part thereof can be configured to be distributed or integrated functionally or physically in arbitrary units according to various kinds of loads, usage conditions, and the like. Furthermore, as for the respective processing functions performed by the respective devices, all or an arbitrary part thereof can be implemented by a CPU and a computer program that is analyzed and executed by the CPU, or can be implemented as hardware by wired logic.

Moreover, all or a part of the processing explained as to be performed automatically out of the respective processing explained in the above embodiments can be performed manually also, while all or a part of the processing explained as to be performed manually can be performed automatically also by a publicly-known method. In addition, the processing procedures, the control procedures, the specific names, and the information including various kinds of data and parameters indicated in the above document and the drawings can be arbitrarily modified unless otherwise specified.

Furthermore, the image processing method explained in the above embodiments can be implemented by executing an image processing program that has been prepared in advance by a computer such as a personal computer and a workstation. This image processing method can be distributed through a network such as the Internet. Furthermore, this image processing program can be stored in a computer-readable recording medium, such as a hard disk, a flexible disk (FD), a compact-disk read-only memory (CD-ROM), a magneto optical disk (MO), and a digital versatile disk (DVD), and can be executed by being read by a computer from the recording medium.

Moreover, substantial real time in the above embodiments means to perform the respective processing soon after each data to be a subject to be processed occurs. That is, the real time is not limited to a case in which a time when a subject is imaged and a time when the image is displayed are completely synchronized, but includes a case in which the image is displayed with a little delay according to time necessary for the image generation processing.

According to at least one of the embodiments explained above, a stereoscopic image in parametric imaging can be provided easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising processing circuitry configured to
    generate plural frames of time-series first vessel image data, whose observation direction is a first observation direction, and generates at least one frame of second vessel image data, whose observation direction is a second observation direction,
    generate plural frames of third vessel image data, whose observation direction is the second observation direction, by transforming more than one frame out of the plural frames of the first vessel image data based on a blood vessel shape in at least one of the plural frames of the first vessel image data and a blood vessel shape in at least one of one frame of the second vessel image data, the third vessel image data corresponding to respective time phases of the plural frames of the first vessel image data,
    generate first color image data, whose observation direction is the first observation direction, and that reflects a flow of a contrast agent by using more than one frame cut of the plural frames of the first vessel image data, and generates second color image data, whose observation direction is the second observation direction, and that reflects the flow of the contrast agent by using more than one frame out of the plural frames of the third vessel image data, and
    cause a display to display a stereoscopic image based on the first color-image data and the second color image data.

2. The X-ray diagnostic apparatus according to claim 1, further comprising:
    an imaging mechanism configured to
       include an X-ray tube generating an X-ray, and a detector detecting the X-ray, and
       hold at least the X-ray tube in a movable manner such that an observation direction by the X-ray is variable; and
    an imaging controller configured to control the observation direction of the imaging mechanism, and imaging performed by the X-ray tube and the detector, wherein
    the imaging controller acquires plural frames of time-series first contrast-image data in a state in which the observation direction of the imaging mechanism is set to the first observation direction, and changes the observation direction of the imaging mechanism to the second observation direction after acquisition of the first contrast image data to acquire at least one frame of second contrast image data, and
    the processing circuitry generates the plural frames of vessel-image data based on the plural frames of the first contrast-image data, and generates at least one frame of the second vessel image data based on the at least one frame of the second contrast-image data.

3. The X-ray diagnostic apparatus according to claim 2, wherein the processing circuitry generates the plural frames of the first vessel image data by subtracting first non-contrast image data, whose observation direction is the first observation direction from each of the plural frames of the first contrast-image data, and generates the at least one frame of the second vessel image data by subtracting second non-contrast image data from the at the least one frame of the second contrast image data.

4. The X-ray diagnostic apparatus according to claim 3, wherein the imaging controller acquires the plural frames of the first contrast image data in predetermined time period from a start of injection of a contrast agent, and shifts to the second observation direction when the predetermined time passes from the start of injection of the contrast agent to acquire the at least one frame of the second contrast-image data.

5. The X-ray diagnostic apparatus according to claim 3, wherein the imaging controller acquires the first contrast image data of a plurality of time phases from a start of injection of a contrast agent, and shifts to the second observation direction before or just after completion of the injection to acquire the second contrast image data.

6. The X-ray diagnostic apparatus according to claim 1, wherein the processing circuitry generates plural frames of the second vessel image data in time-series,
    generates a plurality of fourth vessel image data, whose observation direction is the first observation direction, by transforming more than one frame out of the plural frames of the second vessel image data based on a blood vessel shape in at least one of the plurality of the first vessel image data and a blood vessel shape in at least one of the plurality of the second vessel image data, the fourth vessel image data corresponding to respective time phases of the plurality of pieces of the second vessel image data, and
    generates the first color image data based on more than one frame out of the plurality of the first vessel image data and more than one out of the plurality of the fourth vessel image data, and generates the second color image data based on more than one piece out of the plurality of pieces of the second vessel image data and more than one piece out of the plurality of the third vessel image data.

7. The X-ray diagnostic apparatus according to claim 6, further comprising
    an imaging mechanism configured to
       include an X-ray tube generating an X-ray, and detector detecting the X-ray, and
       hold at least the X-ray tube in a movable manner such that an observation direction by the X-ray is variable, wherein
    the processing circuitry controls the observation direction of the imaging mechanism, and imaging performed by the X-ray tube and the detector,
       acquires plural frames of time-series first contrast-image data and plural frames of time-series second contrast image data by performing imaging while repeatedly switching the observation direction of the imaging mechanism between the first observation direction and the second observation direction, and generates the plural frames of the first vessel image data based on the plurality of the first contrast image data and generates the plural frames of the second vessel image data based on the plural frames of the second contrast- image data.

8. The X-ray diagnostic apparatus according to claim wherein the processing circuitry generates plural frames of the first vessel image data by subtracting non-contrast image data corresponding to the first contrast image data from each of the plural frames of the first contrast image data,
generates plurality of frames of the second vessel image data by subtracting non-contrast image data corresponding to the second contrast image data from each of the plural frames of the second contrast image data,
generates the third vessel image data by subjecting the plurality of the first vessel image data to transformation process, and
generates the fourth vessel-image data by subjecting the plurality of pieces of the second vessel-image data to transformation process.

9. The X-ray diagnostic apparatus according to claim 7, wherein the processing circuitry performs imaging while repeatedly switching the observation direction of the imaging mechanism between the first observation direction and the second observation direction by vibrating the imaging mechanism.

10. An X-ray diagnostic apparatus comprising processing circuitry configured to
generate plural frames of e-series first vessel image data, whose observation direction is a first observation direction, and generates plural frames of time-series second vessel image data, whose observation direction is a second observation direction,
generate plural frames of time-series third vessel image data, whose observation direction is the first observation direction, by transformation using at least one frame out of the plural frames of the first vessel-image data as a reference, the transformation transforming other frames of the plurality of the first vessel-image data,
generate plural frames of time-series fourth-vessel-image data, whose observation direction is the second observation direction, by transformation using at least one frame out of the plural frames of the second vessel-image data as a reference, the transformation transforming other frames of the plurality of the second vessel-image data,
generate first color-image data, whose observation direction is the first observation direction, and that reflects a flow of a contrast agent based on the plural frames of the third vessel-image data, and generates second color-image data, whose observation direction is the second observation direction, and that reflects the flow of the contrast agent based on the plural frames of the fourth vessel-image data, and
cause a display to display a stereoscopic image based on the first color-image data and the second color-image data.

11. An image processing apparatus comprising processing circuitry configured to generate plural frames of time-series first vessel-image data, whose observation direction is a first observation direction, and generates at least one frame of second vessel-image data, whose observation direction is a second observation direction,
generate plural frames of third-vessel image data, whose observation direction is the second observation direction, by transforming more than one frame out of the plural frames of the first vessel-image data based on a blood vessel shape in at least one of the plural frames of the firs vessel-image data and a blood vessel shape in at least one frame of the second vessel-image data, the third-vessel image data corresponding to respective time phases of the plurality of pieces of the first vessel-image data,
generate first color-image data, whose observation direction is a first observation direction, and that reflects a flow of a contrast agent by using more than one frame out of the plural frames of the first vessel-image data, and generates second color-image data, whose observation direction is the second observation direction, and that reflects the flow of the contrast agent by using more than one frame out of the plurality of the third vessel-image data, and
cause a display to display a stereoscopic image based on the first color-image data and the second color-image data.

12. An image processing apparatus comprising processing circuitry generate plural frames of time-series first vessel-image data, whose observation direction is a first observation direction, and generates plural frames of time-series second vessel-image data, whose observation direction is a second observation direction,
generates plural frames of time-series third-vessel image data, whose observation direction is the first observation direction, by transformation using at least one frame out of the plural frames of the first vessel-image data as a reference, the transformation transforming other frames of the plurality of the first vessel-image data,
generate plural frames of time-series fourth-vessel image data, whose observation direction is the second observation direction, by transformation using at least one frame out of the plural frames of the second vessel-image data as a reference, the transformation transforming other frames of the plurality of the second vessel-image data,
generate first color-image data, whose observation direction is the first observation direction, and that reflects a flow of a contrast agent based on the plural frames of the third vessel-image data, and generates second color-image data, whose observation direction is the second observation direction, and that reflects the flow of the contrast agent based on the plural frames of the fourth vessel-image data, and
cause a display to display a stereoscopic image based on the first color-image data and the second color-image data.

13. An image processing method comprising:
generating plural frames of time-series first vessel-image data, whose observation direction is a first observation direction, and generating at least one piece of second vessel-image data, whose observation direction is second observation direction;
generating plural frames of third-vessel image data, whose observation direction is the second observation direction, by transforming more than one piece out of the plural frames of the first vessel-image data based on a blood vessel shape in at least one of the plural frames of the first vessel-image data and a blood vessel shape in at least one frame of the second vessel-image data, the third-vessel image data corresponding to respective time phases of the plural frames of the first vessel-image data;

generating first color-image data, whose observation direction is a first observation direction, and that reflects a flow of a contrast agent by using more than one frame out of the plural frames of the first vessel-image data, and generating second color-image data, whose observation direction is the second observation direction, and that reflects the flow of the contrast agent by using more than one frame out of the plurality of the third vessel-image data; and causing a display to display a stereoscopic image based on the first color-image data and the second color-image data.

14. An image processing method comprising:

generating plural frames of time-series first vessel-image data, whose observation direction is a first observation direction, and generating plural frames of time-series second vessel-image data, whose observation direction is a second observation direction;

generating plural frames of time-series third-vessel image data, whose observation direction is the first observation direction, by transformation using at least one frame cut of the plural frames of the first vessel-image data as a reference, the transformation transforming other frames of the plurality of the first vessel-image data;

generating plural frames of time-series fourth-vessel image data, whose observation direction is the second observation direction, by transformation using at least one frame cut of the plural frames of the second vessel-image data as a reference, the transformation transforming other frames of the plurality of the second vessel-image data;

generating first color-image data, whose observation direction is the first observation direction, and that reflects a flow of a contrast agent based on the plural frames of the third vessel-image data, and generating second color-image data, whose observation direction is the second observation direction, and that reflects the flow of the contrast agent based on the plural frames of the fourth vessel-image data; and causing a display to display a stereoscopic image based on the first color-image data and the second color-image data.

* * * * *